(12) United States Patent
Grandt et al.

(10) Patent No.: US 7,625,353 B2
(45) Date of Patent: Dec. 1, 2009

(54) CATHETER HAVING FIRST AND SECOND GUIDEWIRE TUBES AND OVERLAPPING STIFFENING MEMBERS

(75) Inventors: Axel Grandt, Strassberg (DE); Randolf Von Oepen, Los Altos Hills, CA (US); Thomas Rieth, Hirrlingen (DE)

(73) Assignee: Abbott Laboratories, Abbott Park, IL (US)

( * ) Notice: Subject to any disclaimer, the term of this patent is extended or adjusted under 35 U.S.C. 154(b) by 552 days.

(21) Appl. No.: 11/136,640

(22) Filed: May 23, 2005

(65) Prior Publication Data
US 2005/0267408 A1    Dec. 1, 2005

Related U.S. Application Data

(60) Provisional application No. 60/654,022, filed on Feb. 17, 2005, provisional application No. 60/575,643, filed on May 27, 2004.

(51) Int. Cl.
*A61M 31/00* (2006.01)
(52) U.S. Cl. .............................. 604/103.09; 604/103.04
(58) Field of Classification Search ............ 604/103.04, 604/509, 528, 103.09
See application file for complete search history.

(56) References Cited

U.S. PATENT DOCUMENTS

| 4,490,421 | A |  | 12/1984 | Levy |  |
|---|---|---|---|---|---|
| 4,563,181 | A |  | 1/1986 | Wijayarathna et al. |  |
| 4,721,115 | A | * | 1/1988 | Owens | ........................ 600/526 |
| 4,748,982 | A |  | 6/1988 | Horzewski et al. | .......... 128/344 |
| 4,762,129 | A |  | 8/1988 | Bonzel | ........................ 128/344 |
| 4,771,777 | A |  | 9/1988 | Horzewski et al. | .......... 128/344 |
| RE32,983 | E |  | 7/1989 | Levy |  |
| 4,877,031 | A |  | 10/1989 | Conway et al. | .............. 128/344 |
| 4,892,519 | A |  | 1/1990 | Songer et al. |  |
| 4,898,591 | A |  | 2/1990 | Jang et al. |  |
| 4,921,483 | A |  | 5/1990 | Wijay et al. | .................... 604/96 |

(Continued)

FOREIGN PATENT DOCUMENTS

DE    94 20 821    4/1995

(Continued)

OTHER PUBLICATIONS

Restriction Requirement mailed on Mar. 17, 2008 for U.S. Appl. No. 11/136,251.

(Continued)

*Primary Examiner*—Nicholas D Lucchesi
*Assistant Examiner*—Aarti Bhatia
(74) *Attorney, Agent, or Firm*—Baker Botts L.L.P.

(57) ABSTRACT

The invention includes a catheter having an elongate main body having a proximal section and a distal section. The elongate main body further includes a first guidewire lumen and a second guidewire lumen. Each guide wire lumen including a proximal port and a distal port in communication with an external environment. The proximal port of the first guidewire lumen spaced by a gap from the distal port of the second guidewire lumen. In accordance with a further aspect of the invention, the catheter includes a plurality of overlapping stiffening members defined along at least a portion of a length between the distal end and the proximal end of the elongate main body.

24 Claims, 10 Drawing Sheets

U.S. PATENT DOCUMENTS

| | | | |
|---|---|---|---|
| 4,944,745 A | 7/1990 | Sogard et al. ............... 606/194 |
| RE33,561 E | 3/1991 | Levy |
| 5,037,404 A | 8/1991 | Gold et al. |
| 5,047,045 A | 9/1991 | Arney et al. ............... 606/194 |
| 5,078,702 A | 1/1992 | Pomeranz |
| 5,102,403 A | 4/1992 | Alt ............................ 604/280 |
| 5,135,535 A | 8/1992 | Kramer ..................... 606/194 |
| 5,147,317 A | 9/1992 | Shank et al. |
| 5,154,725 A | 10/1992 | Leopold .................... 606/194 |
| 5,195,978 A | 3/1993 | Schiffer ..................... 604/161 |
| 5,217,482 A | 6/1993 | Keith ........................ 606/194 |
| 5,221,270 A | 6/1993 | Parker |
| 5,226,888 A | 7/1993 | Arney ........................ 604/96 |
| 5,252,159 A | 10/1993 | Arney ........................ 156/169 |
| 5,261,879 A | 11/1993 | Brill ............................ 604/96 |
| 5,267,958 A | 12/1993 | Buchbinder et al. .......... 604/96 |
| 5,304,198 A | 4/1994 | Samson |
| 5,328,468 A | 7/1994 | Kaneko et al. |
| 5,334,147 A | 8/1994 | Johnson ...................... 604/96 |
| 5,357,978 A | 10/1994 | Turk .......................... 128/772 |
| 5,370,615 A | 12/1994 | Johnson ...................... 604/96 |
| 5,395,334 A | 3/1995 | Keith et al. ................. 604/102 |
| 5,410,797 A | 5/1995 | Steinke et al. |
| 5,413,557 A | 5/1995 | Solar .......................... 604/96 |
| 5,413,560 A | 5/1995 | Solar ......................... 604/164 |
| 5,425,711 A | 6/1995 | Ressemann et al. .......... 604/96 |
| 5,443,457 A | 8/1995 | Ginn et al. |
| 5,460,185 A | 10/1995 | Johnson et al. ............. 128/772 |
| 5,470,315 A | 11/1995 | Adams ........................ 604/96 |
| 5,480,383 A | 1/1996 | Bagaoisan et al. ............ 604/96 |
| 5,489,271 A * | 2/1996 | Andersen ............... 604/103.04 |
| 5,490,837 A | 2/1996 | Blaeser et al. |
| 5,496,346 A | 3/1996 | Horzewski et al. .......... 606/194 |
| 5,500,180 A | 3/1996 | Anderson et al. |
| 5,538,510 A | 7/1996 | Fontirroche et al. |
| 5,545,138 A | 8/1996 | Fugoso et al. ............... 604/102 |
| 5,549,553 A | 8/1996 | Ressemann et al. .......... 604/96 |
| 5,549,563 A | 8/1996 | Kronner et al. |
| 5,588,964 A | 12/1996 | Imran et al. |
| 5,605,543 A | 2/1997 | Swanson ..................... 604/96 |
| 5,634,902 A | 6/1997 | Johnson et al. .............. 604/96 |
| 5,649,909 A | 7/1997 | Cornelius .................... 604/96 |
| 5,656,029 A | 8/1997 | Imran et al. |
| 5,658,251 A | 8/1997 | Ressemann et al. ......... 604/102 |
| 5,662,622 A | 9/1997 | Gore et al. |
| 5,667,493 A | 9/1997 | Janacek ....................... 604/96 |
| 5,669,932 A | 9/1997 | Fischell et al. |
| 5,695,483 A | 12/1997 | Samson |
| 5,702,439 A | 12/1997 | Keith et al. .................. 604/96 |
| 5,711,909 A | 1/1998 | Gore et al. |
| 5,728,067 A | 3/1998 | Enger |
| 5,733,400 A | 3/1998 | Gore et al. |
| 5,738,667 A | 4/1998 | Solar ........................... 604/280 |
| 5,755,685 A | 5/1998 | Andersen ...................... 604/53 |
| 5,755,687 A | 5/1998 | Donlon et al. |
| 5,775,685 A | 7/1998 | Yamaoka et al. |
| 5,807,355 A | 9/1998 | Ramzipoor et al. .......... 604/282 |
| 5,820,594 A | 10/1998 | Fontirroche et al. |
| 5,820,613 A | 10/1998 | Van Werven-Franssen et al. |
| 5,823,995 A | 10/1998 | Fitzmaurice et al. |
| 5,824,173 A | 10/1998 | Fontirroche et al. ............ 156/86 |
| 5,833,604 A * | 11/1998 | Houser et al. ................ 600/373 |
| 5,836,965 A | 11/1998 | Jendersee et al. |
| 5,843,032 A | 12/1998 | Kastenhofer ................. 604/96 |
| 5,843,050 A | 12/1998 | Jones et al. |
| 5,851,464 A | 12/1998 | Davila et al. |
| 5,882,336 A | 3/1999 | Janacek et al. |
| 5,891,056 A | 4/1999 | Ramzipoor .................. 600/585 |
| 5,891,110 A | 4/1999 | Larson et al. ................ 604/280 |
| 5,902,290 A | 5/1999 | Peacock, III et al. ......... 604/282 |
| 5,951,539 A | 9/1999 | Nita et al. |
| 5,980,486 A | 11/1999 | Enger .......................... 604/102 |
| 6,004,291 A | 12/1999 | Ressemann et al. ............ 604/96 |
| 6,010,521 A | 1/2000 | Lee et al. |
| 6,017,323 A | 1/2000 | Chee |
| 6,027,477 A | 2/2000 | Kastenhofer ................. 604/96 |
| 6,030,405 A | 2/2000 | Zarbatany et al. ............ 606/191 |
| 6,036,670 A | 3/2000 | Wijeratne et al. .............. 604/96 |
| 6,036,715 A | 3/2000 | Yock ............................ 604/194 |
| 6,059,770 A | 5/2000 | Peacock, III et al. .......... 604/526 |
| 6,066,114 A | 5/2000 | Goodin et al. |
| 6,071,273 A | 6/2000 | Euteneuer et al. ............ 604/523 |
| 6,102,890 A | 8/2000 | Stivland et al. ................ 604/96 |
| 6,123,698 A | 9/2000 | Spears et al. |
| 6,129,708 A | 10/2000 | Enger ...................... 604/103.04 |
| 6,159,229 A | 12/2000 | Jendersee et al. |
| 6,165,166 A | 12/2000 | Samuelson et al. .......... 604/524 |
| 6,187,130 B1 | 2/2001 | Berard et al. |
| 6,193,686 B1 | 2/2001 | Estrada et al. |
| 6,210,364 B1 | 4/2001 | Anderson et al. |
| 6,254,549 B1 | 7/2001 | Ramzipoor |
| 6,273,874 B1 | 8/2001 | Parris .......................... 604/198 |
| 6,273,899 B1 * | 8/2001 | Kramer ....................... 606/194 |
| 6,283,939 B1 | 9/2001 | Anderson et al. |
| 6,306,105 B1 | 10/2001 | Rooney et al. |
| 6,306,124 B1 | 10/2001 | Jones et al. |
| 6,309,402 B1 | 10/2001 | Jendersee et al. |
| 6,319,244 B2 | 11/2001 | Suresh et al. |
| 6,344,029 B1 | 2/2002 | Estrada et al. |
| 6,361,529 B1 | 3/2002 | Goodin et al. ............... 604/524 |
| 6,368,302 B1 | 4/2002 | Fitzmaurice et al. ... 604/103.04 |
| 6,402,720 B1 | 6/2002 | Miller et al. |
| 6,475,184 B1 | 11/2002 | Bruce et al. |
| 6,475,209 B1 | 11/2002 | Larson et al. ................ 604/525 |
| 6,488,694 B1 | 12/2002 | Lau et al. ..................... 606/194 |
| 6,527,789 B1 | 3/2003 | Lau et al. ..................... 606/194 |
| 6,530,938 B1 | 3/2003 | Lee et al. |
| 6,565,588 B1 | 5/2003 | Clement et al. |
| 6,575,958 B1 | 6/2003 | Happ et al. ................... 604/525 |
| 6,575,993 B1 | 6/2003 | Yock ........................... 606/194 |
| 6,579,278 B1 | 6/2003 | Bencini |
| 6,633,648 B1 | 10/2003 | Bauck |
| 6,648,854 B1 | 11/2003 | Patterson et al. |
| 6,652,507 B2 | 11/2003 | Pepin |
| 6,663,648 B1 | 12/2003 | Trotta ......................... 606/194 |
| 6,685,720 B1 | 2/2004 | Wu et al. ..................... 606/192 |
| 6,685,721 B1 * | 2/2004 | Kramer ....................... 606/194 |
| 6,692,460 B1 | 2/2004 | Jayaraman ............. 604/102.02 |
| 6,695,812 B2 | 2/2004 | Estrada et al. ......... 604/103.09 |
| 6,702,750 B2 | 3/2004 | Yock ........................... 600/467 |
| 6,702,781 B1 * | 3/2004 | Reifart et al. .............. 604/96.01 |
| 6,733,473 B1 | 5/2004 | Reifart et al. .............. 604/96.01 |
| 6,733,487 B2 | 5/2004 | Keith et al. .................. 604/526 |
| 6,770,038 B2 | 8/2004 | Balbierz et al. |
| 6,814,744 B2 | 11/2004 | Yang et al. |
| 6,818,001 B2 | 11/2004 | Wulfman et al. |
| 6,821,281 B2 | 11/2004 | Sherman et al. |
| 6,821,287 B1 | 11/2004 | Jang ............................ 606/194 |
| 6,887,219 B2 | 5/2005 | Wantink .................. 604/103.04 |
| 6,893,417 B2 | 5/2005 | Gribbons et al. |
| 6,979,342 B2 | 12/2005 | Lee et al. |
| 7,001,358 B2 | 2/2006 | Fitzmaurice et al. |
| 7,025,258 B2 | 4/2006 | Chang |
| 7,037,291 B2 | 5/2006 | Lee et al. |
| 7,118,551 B1 | 10/2006 | Lee et al. |
| 7,309,334 B2 | 12/2007 | Von Hoffmann |
| 2001/0021840 A1 | 9/2001 | Suresh et al. |
| 2001/0034514 A1 | 10/2001 | Parker |
| 2002/0007146 A1 | 1/2002 | Omaleki et al. |
| 2003/0105427 A1 | 6/2003 | Lee et al. ............... 604/103.04 |
| 2003/0163082 A1 | 8/2003 | Mertens |
| 2004/0010243 A1 | 1/2004 | Klint |
| 2004/0019322 A1 | 1/2004 | Hoffmann |
| 2004/0193140 A1 | 9/2004 | Griffin et al. |

| | | | |
|---|---|---|---|
| 2004/0236367 | A1 | 11/2004 | Brown et al. ............... 606/194 |
| 2005/0059292 | A1 | 3/2005 | Hayashi et al. |
| 2005/0131387 | A1 | 6/2005 | Pursley |
| 2006/0270977 | A1 | 11/2006 | Fisher et al. |
| 2007/0167913 | A1 | 7/2007 | Elkins et al. |

FOREIGN PATENT DOCUMENTS

| | | |
|---|---|---|
| DE | 197 29 499 A1 | 1/1999 |
| EP | 0 029 185 A | 5/1981 |
| EP | 0 408 198 | 1/1991 |
| EP | 0 414 350 | 2/1991 |
| EP | 0518205 A | 12/1992 |
| EP | 0 806 220 A | 11/1997 |
| EP | 0 916 359 | 5/1999 |
| EP | 1 435 252 | 7/2004 |
| EP | 1 518 581 | 3/2005 |
| WO | WO/92/17236 | 10/1992 |
| WO | WO 98/56448 | 12/1998 |
| WO | WO 01/070321 | 9/2001 |
| WO | WO/2005/118044 | 5/2005 |
| WO | WO/2005/118045 | 5/2005 |
| WO | WO 2005/113047 | 12/2005 |
| WO | WO/2006/104591 | 2/2006 |

OTHER PUBLICATIONS

Response to the Restriction Requirement filed on Apr. 14, 2008 for U.S. Appl. No. 11/136,251.
Non-Final Rejection mailed on Jun. 2, 2008 for U.S. Appl. No. 11/136,251.
Response to the non-Final Rejection mailed on Jun. 2, 2008 filed on Sep. 2, 2008 for U.S. Appl. No. 11/136,251.
Examiner Interview Summary Record mailed on Dec. 17, 2008 for U.S. Appl. No. 11/136,251.
Interview Summary and Supplemental Amendment filed on Dec. 19, 2008 for U.S. Appl. No. 11/136,251.
Notice of Allowance mailed on Jan. 13, 2009 for U.S. Appl. No. 11/136,251.
Issue Fee Payment received on Mar. 20, 2009 for U.S. Appl. No. 11/136,251.
Non-Final Rejection mailed on Nov. 3, 2008 for U.S. Appl. No. 11/357,775.
Response to the non-Final Rejection mailed on Nov. 3, 2008 filed on Feb. 3, 2009 for U.S. Appl. No. 11/357,775.
Final Rejection mailed on May 18, 2009 for U.S. Appl. No. 11/357,775.
Request for Continued Examination (RCE) and Amendment after Final Rejection filed on Aug. 17, 2009 for U.S. Appl. No. 11/357,775.
Preliminary Amendment filed on Aug. 18, 2006 for U.S. Appl. No. 11/439,809.
Restriction Requirement mailed on Jul. 29, 2008 for U.S. Appl. No. 11/439,809.
Response to the Restriction Requirement filed on Aug. 25, 2008 for U.S. Appl. No. 11/439,809.
Non-Final Rejection mailed on Sep. 3, 2008 for U.S. Appl. No. 11/439,809.
Notice of Abandoment mailed on May 1, 2009 for U.S. Appl. No. 11/439,809.
Non-Final Rejection mailed on Nov. 14, 2008 for U.S. Appl. No. 11/439,591.
Response to the non-Final Rejection mailed on Nov. 14, 2008 filed on Feb. 17, 2009 for U.S. Appl. No. 11/439,591.
Notice of Non-Compliant Amendment mailed on Mar. 25, 2009 for U.S. Appl. No. 11/439,591.
Response to the non-Final Rejection mailed on Nov. 14, 2008 filed on Apr. 16, 2009 for U.S. Appl. No. 11/439,591.
Final Rejection mailed on Jul. 24, 2009 for U.S. Appl. No. 11/439,591.
Non-Final Rejection mailed on Nov. 4, 2008 for U.S. Appl. No. 11/439,592.
Response to the non-Final Rejection mailed on Nov. 4, 2008 filed on Feb. 4, 2009 for U.S. Appl. No. 11/439,592.
Final Rejection mailed on May 19, 2009 for U.S. Appl. No. 11/439,592.
Request for Continued Examination (RCE) and Amendment after Final Rejection filed on Aug. 17, 2009 for U.S. Appl. No. 11/439,592.
Preliminary Amendment filed on Aug. 18. 2006 for U.S. Appl. No. 11/439,596.

* cited by examiner

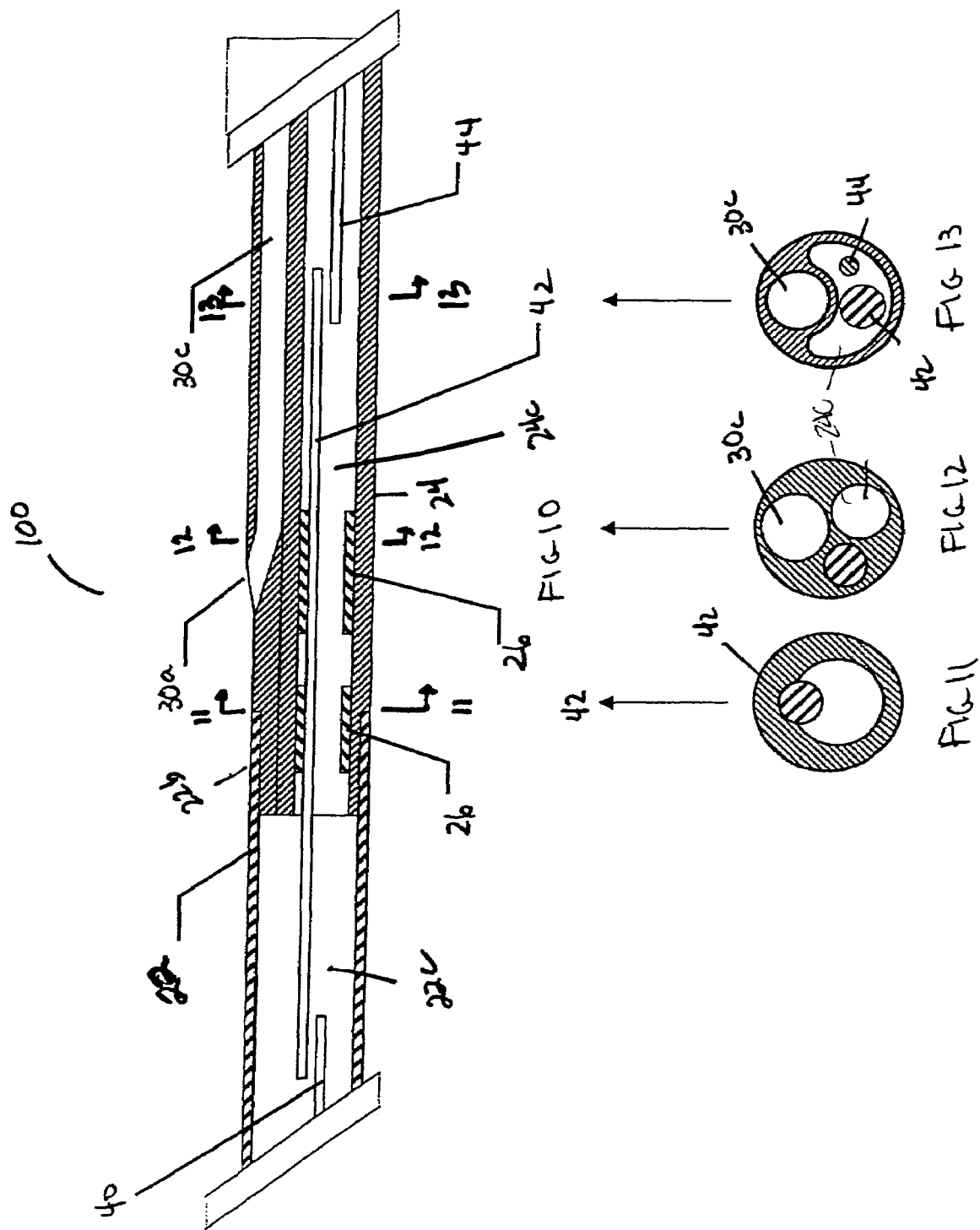

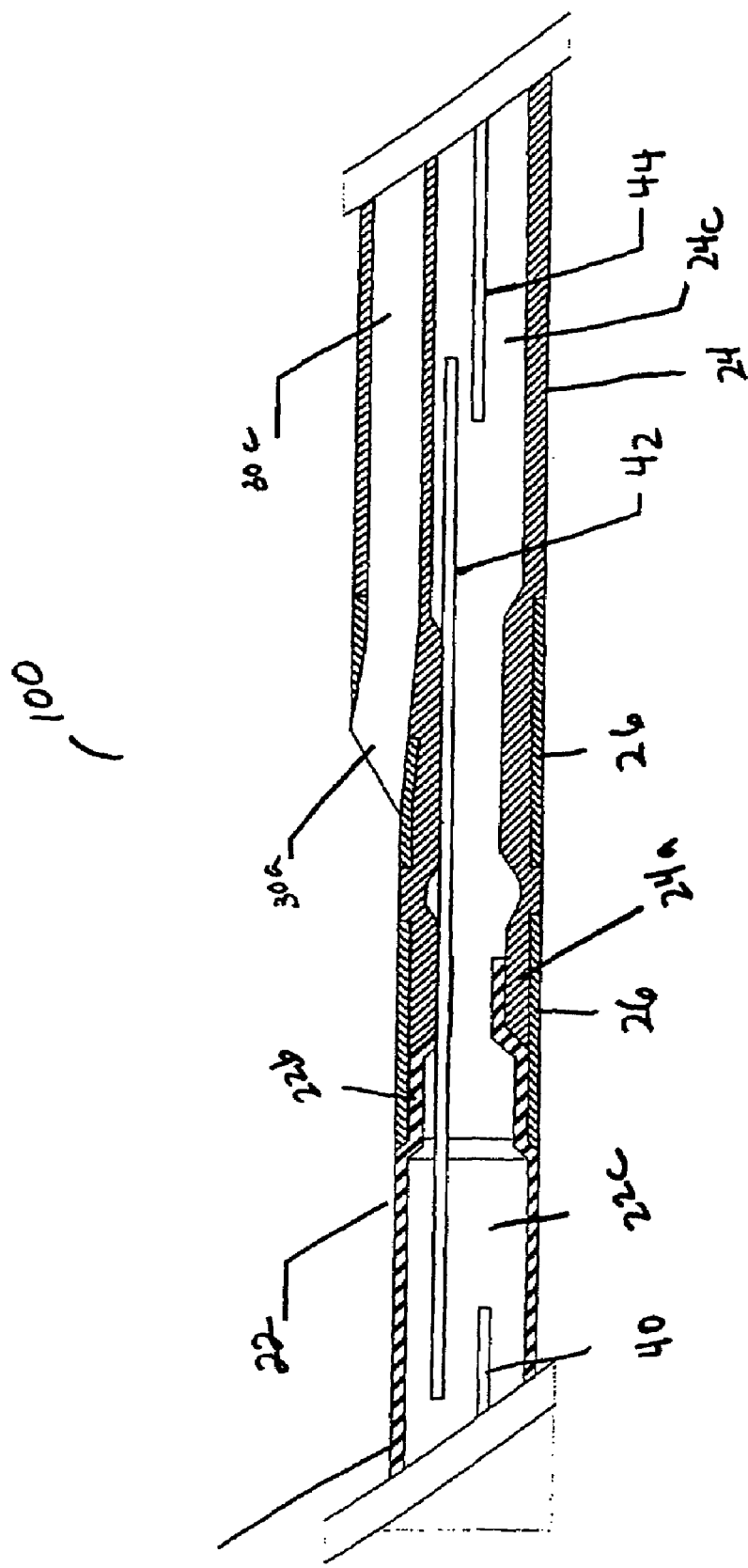

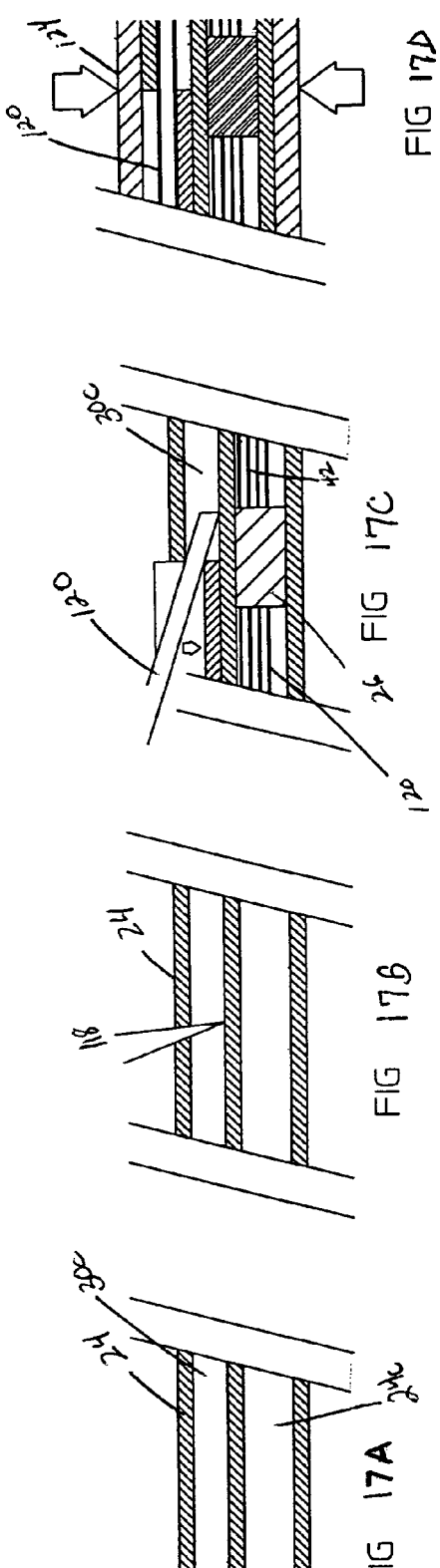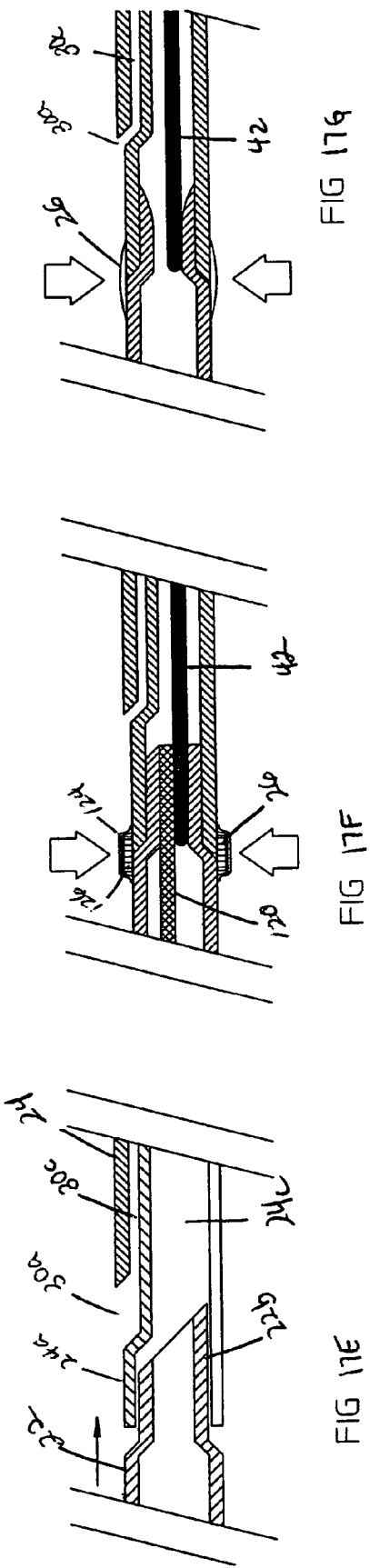

CATHETER HAVING FIRST AND SECOND GUIDEWIRE TUBES AND OVERLAPPING STIFFENING MEMBERS

CROSS-REFERENCE

The present application claims the benefit of U.S. Provisional Patent Application Ser. No. 60/575,643 filed on May 27, 2004, and Ser. No. 60/654,022 filed on Feb. 17, 2005, the entire contents of each are incorporated herein by reference.

BACKGROUND OF THE INVENTION

1. Field of the Invention

The present invention relates to a catheter for treating a luminal system of a patient. Particularly, the present invention is directed to a rapid exchange catheter having a first guidewire tube and a second guidewire tube. Moreover, the present invention provides an improved rapid exchange type catheter.

2. Description of Related Art

A variety of catheter devices are known in the art for treating the luminal system of a patient. Of such devices, many are directed to treating the cardiovascular system of a patient.

"Over-the-wire" catheters are generally known in the art. Such catheters are generally introduced into a patient after a guidewire has been introduced into the patient, and advanced to a treatment site within a patient where a diagnostic, interventional or other treatment procedure (e.g., angioplasty and/or stent placement) is to be performed. The catheter is advanced over-the-guidewire to the treatment site, the treatment procedure is performed, and the catheter and guidewire are subsequently removed. Such systems can be disadvantageous. Because the guidewire lumen of an over the wire catheter must traverse the entire length of the catheter (which is normally about 145 cm), either an extremely long guidewire (greater than 300 cm in length) or a guidewire extension must be used to permit the physician to maintain a grip on the guidewire and catheter during the treatment procedure.

To address this problem, rapid exchange catheters have been developed. Generally, a rapid exchange catheter has a relatively short guidewire lumen (e.g., less than 25 cm) near the distal end of the catheter, thus permitting the physician to use a standard length guidewire (e.g., 180-195 cm) to introduce a catheter and/or perform a catheter exchange.

Such conventional methods and systems generally have been considered satisfactory for their intended purpose. However, rapid exchange catheters still suffer from certain performance issues, such as a lack of pushability and kink resistance. Although solutions to this problem have been developed, such as by introducing metallic components (e.g., hypotubes) along a length of the catheter that is not supported by a guidewire, as well as, configuring the metallic component so that it at least partially overlaps a portion of the guidewire, there still remains a continued need in the art for a catheter having enhanced pushability, kink resistance and versatility. The present invention provides a solution for these problems.

SUMMARY OF THE INVENTION

The purpose and advantages of the present invention will be set forth in and apparent from the description that follows, as well as will be learned by practice of the invention. Additional advantages of the invention will be realized and attained by the methods and systems particularly pointed out in the written description and claims hereof, as well as from the appended drawings.

To achieve these and other advantages and in accordance with the purpose of the invention, as embodied herein and broadly described, the invention includes a catheter having an elongate main body having a proximal end and a distal end. The elongate main body has a proximal section, a distal section, and an intermediate section disposed between the proximal and distal sections. The elongate main body further includes a first guidewire tube having a first guide wire lumen being defined therethrough, and a second guidewire tube having a second guide wire lumen being defined therethrough. Each of the first guidewire lumen and the second guidewire lumen, respectively, has a distal guidewire port and a proximal guidewire port in fluid communication therewith. The proximal guidewire port of the first guidewire lumen is spaced distal to the distal guidewire port of the second guidewire lumen.

In further accordance with the invention, the elongate main body can further include a first segment having structure defining the second guidewire lumen and an inflation lumen configured in a side-by-side arrangement along at least a portion of the length thereof, and a second segment having a structure defining the first guidewire lumen and an inflation member configured in a coaxial arrangement. The second segment is disposed distal to the first segment.

In accordance with still a further aspect of the invention, the catheter can include a plurality stiffening members, collectively, configured to traverse substantially the entire length of the elongate main body. Preferably, the elongate main body can include a proximal stiffening member, intermediate stiffening member and a distal stiffening member. Alternatively, the elongate main body can include a proximal stiffening member and a distal stiffening member. The proximal and distal stiffening members, collectively, can be configured to traverse at least a portion of the length of the elongate main body. As yet another alternative, the catheter can include one stiffening member disposed along a length of the elongate main body.

The plurality of stiffening members can be configured to have an overlapping arrangement, wherein the distal stiffening member has a proximal end that overlaps at least a portion of the intermediate stiffening member, and the intermediate stiffening member has a proximal end that overlaps at least a portion of the proximal stiffening member. If an intermediate stiffening member is not utilized, the stiffening members can be configured so that the distal stiffening member extends proximally and overlaps with at least a portion of the proximal stiffening member. Furthermore, at least one stiffening member can be configured to cross at least one guidewire port.

In accordance with a further aspect of the invention, the stiffness of the elongate main body can vary along its length. The variation can occur over the entire length of the elongate main body, or a portion thereof. The stiffness variation can occur along the length of the elongate main body portion traversed by at least one stiffening member. In accordance with this aspect of the invention, the stiffness of the catheter can be varied by varying the number or length of each stiffening member, or by varying the particular material or dimensions of the stiffening member, including but not limited to its cross-sectional dimension. For example, depending on the stiffness desired, at least one stiffening member can be made of suitable material such as a metal including stainless steel, nitinol, or other metal alloys, as well as polymers, carbon, or fiber reinforced materials, including but not limited to carbon-reinforced material, glass reinforced material, aramid reinforced material and boron fiber reinforced material. For example and not limitation, the proximal stiffening member can include a stainless steel wire, the intermediate stiffening member can include a carbon wire, and the distal stiffening member can include a nitinol wire.

As yet another alternative, the flexibility or bending stiffness of the catheter or a portion of the catheter can be varied depending on the orientation of the stiffening member and the catheter portion. For example, if the stiffening member is oriented such that it is centrally located within a lumen of a tubular member, the stiffness of the tubular member would be relatively uniform across the length of the tubular member when the tubular member is in a bending orientation. However, if the stiffening member is attached or secured to the inner wall of the tubular member, the tubular member would have a variation in stiffness along its length depending on the direction the catheter is bent.

In accordance with a further aspect of the invention, the catheter can further include at least one reinforcement member to reinforce a section of the elongate main body. The at least one reinforcement member can be disposed adjacent to or near at least one guidewire port disposed across the elongate main body. In one embodiment, the reinforcement member can be added to the elongate main body to reinforce the elongated main body at a welding area. Alternatively, the at least one reinforcement member can be disposed between two components along the elongate main body at a welding region to secure the components of the elongated main body and tightly seal the welding region. The reinforcement member can provide added material to the wall of the elongate main body and help to avoid thinning of the wall of the elongate main body during welding or other processes. Avoidance of wall thinning of the elongate main body therefore provides a tight seal, even when high pressure is applied in the lumen of the elongate main body. Accordingly, in one embodiment, the reinforcement member is a sealing member to seal a section of the elongate main body. The reinforcing member can be, for example, a tubular member or filler material.

In accordance with another aspect of the invention, the elongate main body can further include an inflatable member. In accordance with this aspect of the invention, an inflation lumen is defined along at least a length of the elongate main body, wherein the inflation lumen is in fluid communication with the inflatable member.

The invention also includes a method of performing an medical procedure. The method includes providing a catheter as described herein, disposing a guidewire within a lumen of a patient, inserting the guidewire through the first guidewire lumen of the elongate main body and the second guidewire lumen of the elongate main body, and positioning the catheter along a length of the guidewire. Alternatively, the method can include inserting the guidewire through only the first guidewire lumen and positioning the catheter along a length of the guidewire.

The method in accordance with the invention can include providing and inflating an inflatable member in a lumen of a patient, retracting the guidewire until a distal extremity of the guidewire is proximal to the proximal guidewire port of the distal end portion of the catheter, and allowing blood to perfuse through the guidewire lumen of the distal body portion. Moreover, the method can include a guidewire lumen configured so that blood can perfuse through the guidewire lumen even with the guidewire disposed in the guidewire lumen, if desired.

It is to be understood that both the foregoing general description and the following detailed description are exemplary and are intended to provide further explanation of the invention claimed.

The accompanying drawings, which are incorporated in and constitute part of this specification, are included to illustrate and provide a further understanding of the method and system of the invention. Together with the description, the drawings serve to explain the principles of the invention.

BRIEF DESCRIPTION OF THE DRAWINGS

FIG. 10 is a schematic side view of another representative embodiment of a catheter in accordance with the present invention;

FIG. 11 is a cross sectional view at line 11-11 of the catheter of FIG. 10 in accordance with the present invention;

FIG. 12 is a cross sectional view at line 12-12 of the catheter of FIG. 10 in accordance with the present invention;

FIG. 13 is a cross sectional view at line 13-13 of the catheter of FIG. 10 in accordance with the present invention;

FIG. 15 is a schematic side view of another embodiment of a catheter in accordance with the present invention;

FIG. 17A to 17G is a schematic representation of a method to manufacture the catheter of FIG. 10 in accordance with the present invention.

DETAILED DESCRIPTION OF THE PREFERRED EMBODIMENT

Reference will now be made in detail to the present preferred embodiments of the invention, an example of which is illustrated in the accompanying drawings. The method and corresponding steps of the invention will be described in conjunction with the detailed description of the system.

The devices and methods presented herein may be used for treating the luminal systems of a patient. The present invention is particularly suited for treatment of the cardiovascular system, including the peripheral vessels of a patient, such as performance of angioplasty or delivery of balloon-expandable or self-expanding interventional devices (e.g., stents, filters, coils). The system treated includes treatment of the peripheral vessels, such as but not limited to carotid, popliteal and renal vessels. Accordingly, the present invention is also suitable for special endovascular vessels.

In accordance with the invention, a catheter is provided having an elongate main body. Generally, the elongate main body has a proximal section, an intermediate section, and a distal section. The catheter further includes first guidewire tube and second guidewire tube. The catheter can further include at least at least two overlapping stiffening members.

Figure 1:
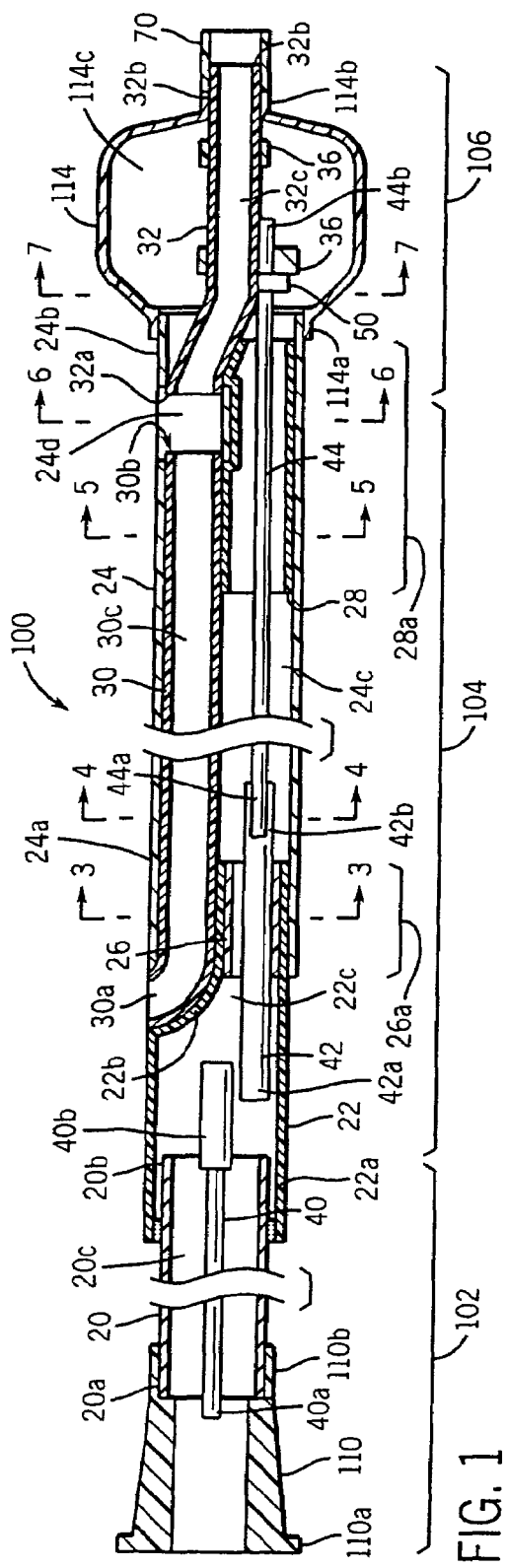
FIG. 1 is a schematic side view of a first representative embodiment of a catheter having a main body portion including a proximal section, intermediate section, and distal section in accordance with the present invention.

For purpose of explanation and illustration, and not limitation, an exemplary embodiment of the catheter in accordance with the invention is shown in FIG. 1 and is designated generally by reference character 100. Additional features, aspects and embodiments of a catheter in accordance with the invention are provided in FIGS. 2-16, as will be described.

For purposes of illustration and not limitation, as embodied herein and as depicted in FIG. 1, catheter 100 has a main body portion including a proximal section 102, a distal section 106, and an intermediate section 104 disposed between the proximal and distal sections. Each section having a proximal end and a distal end.

Generally, the proximal section of the catheter 100 includes adapter 110 secured to proximal tubular member 20. Proximal tubular member 20 has a body including an outer surface, proximal end region 20a, distal end region 20b and inflation lumen 20c therebetween. Proximal end region 20a of proximal tubular member 20 is secured to adapter 110 by suitable structure or method. For example and not limitation, proximal tubular member can be affixed to adapter 110 by fusion, welding, overmolding, e.g., injection molding, or adhesive.

Additionally, and as schematically depicted in FIG. 1, adapter 110 can have a distal end 110b in overlapping relation with a portion of proximal tubular member 20. Adapter 110 can be a hub or a handle, a manifold, or can be a luer fitting for connection with an inflation/deflation device, such as a syringe (not shown).

Proximal tubular member 20 can be made of any suitable material, such as metal, metal alloy, carbon, carbon reinforced materials, metal reinforced polymers, boron fiber reinforced materials, glass reinforced materials, aramid fiber reinforced materials, ceramic, composite, Kevlar, or polymer as described further below. The method of joining the adapter 110 and proximal tubular member 20 will depend on the materials used. Preferably, proximal tubular member 20 further includes lumen 20c extending therethrough in fluid communication with adapter 110.

If desired, catheter 100 can include a strain relief (not shown), which extends from adapter 110 and is disposed along at least a portion of proximal tubular member 20 to provide increased resistance to kinking between the adapter and the proximal tubular member. The strain relief is preferably formed of a polymeric material and extends distally along at least a length of proximal tubular member 20. The strain relief can be formed as a separate sleeve, or overmolded onto the proximal tubular member 20. A variety of materials can be used for the strain relief including polymers such as but not limited to FEP, PTFE, polyamide, and PEEK, and metals such as but not limited to stainless steel, and nitinol, e.g., spring.

The method or structure for joining proximal tubular member 20 to intermediate tubular member 22 will depend upon the materials used. For example, adhesive, welding, fusion, RF bonding, or other bonding techniques can be employed. Particularly, if the proximal tubular member is formed from metal and the adjacent tubular member is formed from a polymeric material, the polymeric tubular member can be joined to the metallic tubular member by utilization of a compression tool such as but not limited to a jaw press.

In one preferred embodiment, proximal tubular member 20 is a hypotube made of metal, such as stainless steel, and intermediate tubular member is a polymer, such as nylon. In this embodiment, distal region 20b includes an outer surface having a bonding region defined by a roughened outer surface across a length of the proximal tubular member(not shown). The roughened outer surface can be prepared by for example grit blasting or knurling a portion of the outer surface known techniques. Preferably the bonding region has a length of at least approximately 10 to 20 mm to facilitate securing an adjacent tubular member to proximal tubular member 20. The bonding region can be provided at the distal end of the proximal tubular member 20 or, if desired, can be spaced proximal from the distal end. In further accordance with this embodiment, proximal region 22a of intermediate tubular member 22 can be configured to overlap at least a portion of the bonding region disposed on the outer surface of proximal tubular member 20. For example, and not limitation, intermediate member can overlap the entire length of the bonding region defined by the roughened surface or a portion thereof.

Figure 2:
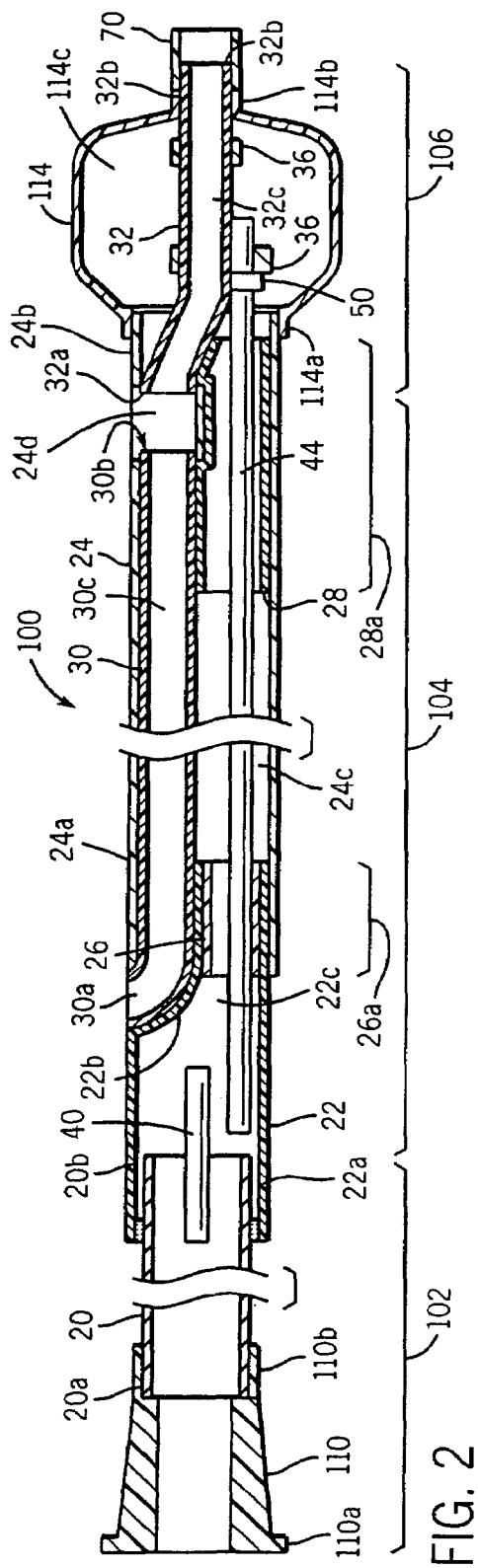
FIG. 2 is a schematic side view of another representative embodiment of a catheter having a main body portion including a proximal body section, an intermediate body section, and a distal body section.

Distal region 20b is secured to an adjacent tubular member, such as intermediate tubular member 22, as depicted in FIGS. 1 and 2, by suitable structure or method. As shown schematically in FIG. 1, proximal end region 22a of intermediate tubular member 22 can be configured to form a lap joint such that proximal end region 22a includes a proximal end that overlaps at least a portion of the distal end region 20b of proximal tubular member 20.

Similarly, it is not required that the bond securing proximal tubular member to intermediate tubular member have a length equivalent to the length of the roughened surface. For the purpose of illustration and not limitation, the proximal region of intermediate member can be configured to overlap an entire length of the roughened surface, for example 10 cm, but have a bonding length of only about 1 cm in the proximal portion of the bonding region length. Accordingly, the intermediate tubular member 22 can be configured to bond to only a portion of the bonding region that is proximate a distal end the bonding region.

Alternatively, the proximal end of intermediate tubular member 22 can be configured to form a butt joint with the distal end of proximal tubular member 20, if desired. In this manner, a polymeric sleeve can be disposed over the junction defined by the butt joint to assist securing the proximal tubular member 20 to the intermediate tubular member 22, if necessary.

A variety of bonding techniques may be utilized to secure intermediate tubular member 22 to the bonding region of proximal tubular member 20. For example, and not limitation, fusion bonding, adhesive, welding, and the like can be used.

A variety of materials can be used for proximal tubular member 20. Proximal tubular member 20 is preferably formed at least in part of a suitable metallic material, such as a metallic hypotube. For example, and not limitation, various metals can be used including stainless steel, nitinol, and other metal alloys. If stainless steel is used, preferably austenitic stainless steel is used.

In accordance with another aspect of the invention, the proximal tubular member 20 can be made of a pure carbon material, polymeric material, fiber reinforced materials such as carbon fiber reinforced material, glass fiber reinforced material, boron fiber reinforced material, Kevlar, metal or metal alloy. The metal or metal alloy is preferably MRI compatible, such as but not limited to niobium, tantalum, tungsten, or any variety of other paramagnetic metals. The use of such materials having sufficiently high compressive strength for proximal tubular member 20 is particularly advantageous to enhance pushability and provide kink resistance for rapid-exchange applications. If desired, the proximal tubular member 20 can further include a lubricious coating, such as a polytetrafluoroethylene or an HDPE coating. Alternative lubricious materials can be used, however, as known in the art. The proximal tube can also be coated with a hydrophilic or a hydrophobic coating to reduce friction, for example and not limitation, the hydrophobic coating can be silicone coating or the like, and the hydrophilic coating can be apolyvinylpyrrolidone or polyacrylamide coating.

Proximal tubular member 20 can also be formed of suitable polymeric material such as PEEK or other relatively stiff polymeric material. Alternatively, proximal tubular member 20 can be formed of a composite member or formed member comprising a fabrication of different materials, such as reinforced polymer materials, or an extrusion or pultrusion of different polymers, if desired. The composite member or formed member can also be formed by a dip molding process, in which a mandrel is dipped into a polymer material, which is dissolved in a suitable solvent, dried, and then re-dipped into another polymer material to form a multi-layered polymeric composite or formed member. As yet another alternative, the composite member or formed member can be formed by applying a second polymeric tube about a first polymeric tube, applying a shrink tubing about first and second polymeric tube assembly and heating the assembly to fuse the first and second tubular members to each other. For each process for forming the composite or formed member described above, the outer surface of the inner polymeric tube can be roughened by mechanical or chemical means to improve the bond between the inner and outer tubular members. For example, the outer surface can be roughened by mechanical means including grinding, sandblasting, or Laser-ablation, or chemical means including etching and leaching.

The composite member can also include a polymeric tubular member loaded with particles of a different polymer. For example and not limitation, a PEEK or polyimide tubular member can be loaded with PTFE particles. In this manner, the PTFE particles can be electrostatically charged such that an electrostatic force bonds the PTFE particles to the PEEK tubular member. A polymeric outer layer, such as nylon tube, can be applied to the PTFE loaded tubular member to form a multi-material, multi-layer composite tubular member. Alternatively, the proximal tubular member can be a fiber-reinforced composite material such as fiber-reinforced resin material including but not limited to carbon reinforced material, glass reinforced material and boron reinforced material, or a liquid crystal reinforced material. Further, to achieve suitable stiffness of the proximal tubular member, a polymeric tubular member can include a metallic element disposed in the inner lumen of the polymeric tubular member, as will be discussed further below.

Generally, the proximal tubular member 20 can have a length of about 100 to about 115 cm. For example and not limitation, the proximal tubular member can be configured to have an outer diameter approximately 0.70 mm and an internal diameter of about 0.52 mm. However, as known in the art, the length and dimensions of the proximal tubular member can be varied depending on the size and location of the lumen (s) to be traversed by the catheter 100. For example, the proximal tubular member can be configured to have smaller dimensions, e.g., outer diameter and internal diameter, if the catheter is used to treat vessels in the brain or extremities of a patient.

Intermediate tubular member includes a distal end region 22b, and preferably further includes lumen 22c defined between distal end region 22b and proximal end region 22a. As previously mentioned, proximal end region 22a is secured to at least a portion of proximal tubular member 20, preferably at a bonding region defined by a roughened outer surface. Lumen 22c is thus in fluid communication with lumen 20c.

A variety of materials can be used for intermediate tubular member 22. For example, intermediate tubular member 22 can be made from any suitable polymer material such as polyamide, PEEK, PEBAX®, PTFE, PVDF, polyimide, polyethylene, polyester, polyurethane, or liquid crystal polymers of various suitable densities. As a further exemplary alternative, intermediate tubular member 22 can be a composite member or formed member comprising a fabrication of several different materials. For example and as described above in detail, the composite or formed member can be made by extrusion or pultrusion of different polymers, if desired. Alternatively, the composite member can be formed by dip molding, applying a first polymeric tubing within a second tubular member and fusing the assembly, or by a loading the polymer tubular member with particles of a different polymer, e.g., PEEK or polyimide tubular member loaded with PTFE particles, as described above. As yet another alternative, the intermediate tubular member can be formed from a fiber-reinforced material, such as fiber-reinforced resin material, e.g., carbon, glass, aramid, boron, or a liquid crystal reinforced material.

The dimensions of the intermediate tubular member 22 will depend upon the intended application. For example, for a cardiovascular catheter, the intermediate tubular member 22 can have a length of at least approximately 10 cm, although a greater length can be used to accommodate an overlap joint with the proximal tubular member 20. For example, and not limitation, the intermediate tubular member can have an outer diameter of approximately 0.85 mm and an inner diameter of approximately 0.70 mm. However, as will be recognized in the art, the intermediate tubular member 22 can be configured with alternate lengths and dimensions, if desired.

In further accordance the invention, and as demonstrated in FIGS. 1 and 2, catheter 100 can further include a distal tubular member 24. Distal tubular member 24 has a proximal end region 24a, a distal end region 24b, and lumen 24c therebetween, and extends distally from intermediate tubular member 22 to distal section 106. The distal shaft lumen 24c is in fluid communication with lumen 22c of intermediates tubular member 22. Accordingly, an inflation lumen can be defined across a substantial length of catheter 100. If both are provided, intermediate tubular member 22 and distal tubular member 24 together thus define the intermediate section 104 of the catheter 100.

Figure 8:
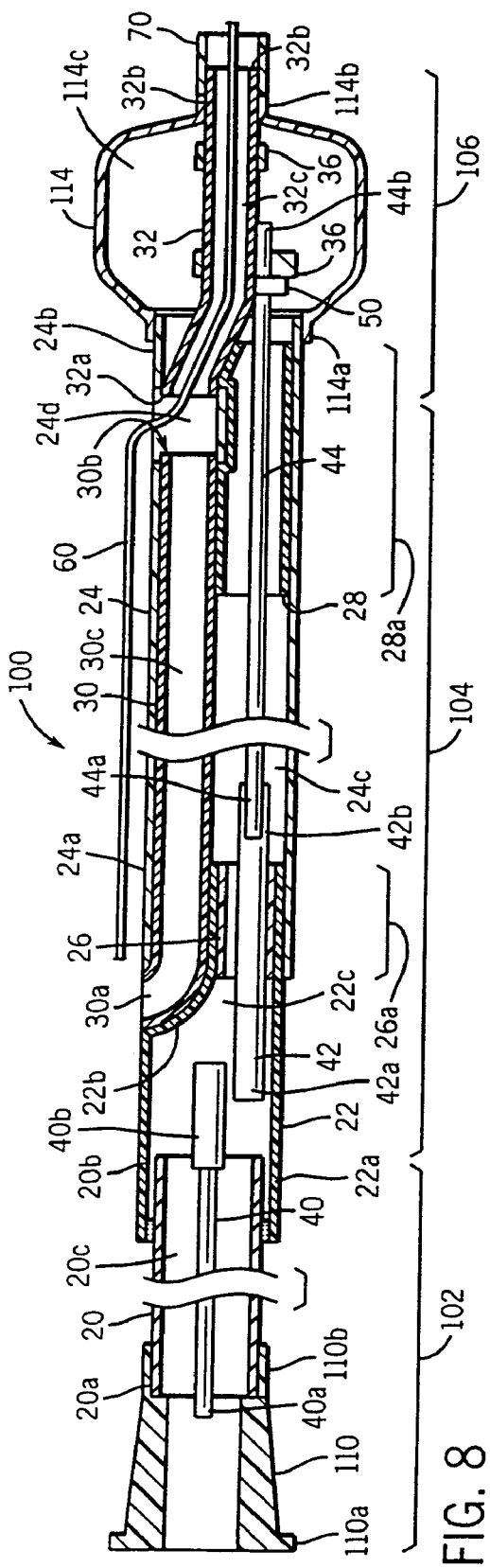
FIG. 8 is a side view of the catheter of FIG. 1 including a guidewire disposed in a first guidewire tube.
Figure 9:
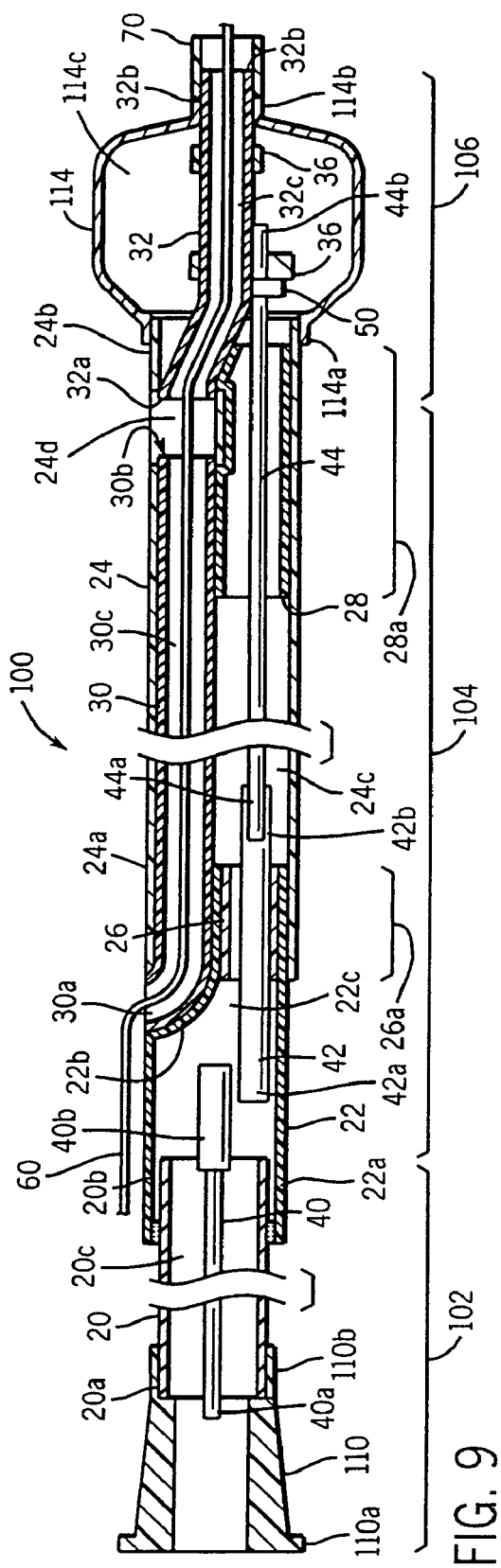
FIG. 9 is a side view of the catheter of FIG. 9 including the guidewire disposed in each of first and second guidewire tubes in accordance with the invention.

As shown in each of FIGS. 1, 8, and 9, a proximal end region 24a of distal tubular member 24 can be secured to at least a portion of distal region 22b of intermediate tubular member 22, as well as to at least a portion of a guidewire tube 30.

A variety of materials and dimensions can be used for distal tubular member 24. Indeed, if both an intermediate tubular member and a distal tubular member are provided, the two members can be formed of the same material and substantially the same cross section dimensions for uniform stiffness and flexibility, or even formed together as a single piece. Alternatively, the distal tubular member 24 can be formed of a different material and/or dimensions to vary flexibility along the length of the catheter. For example, distal tubular member 24 can be made from any suitable polymer material such as polyamide, PEEK, PTFE, PVDF, PEBAX®, polyimide, polyester, polyurethane, liquid crystal polymer, or polyethylene of various suitable densities. As a further exemplary alternative, distal tubular member 24 can be a composite member or formed member comprising a fabrication of several different materials, such as a co-extrusion or pultrusion of different polymers. Alternatively, the composite or formed member can be made by the dip molding process, polymer loading process, or by fusing first and second tubular members to each other, as described in detail above. Alternatively, the distal tubular member can be a fiber-reinforced material such as fiber-reinforced resin material, e.g., carbon, glass, aramid, or boron, or liquid crystal reinforced material.

The dimensions of distal tubular member 24 will depend upon the intended application. For example, for a cardiovascular catheter, the distal tubular member 24 can have a length of approximately 10 to 30 cm, and preferably has a length of approximately 21 to 23 cm. For example, and not limitation, the distal tubular member can have an outer diameter of at least approximately 0.80 mm and an inner diameter of at least approximately 0.68 mm. However, as will be recognized in the art, the distal tubular member 24 can be configured with alternate lengths and dimensions, if desired.

In an alternate construction, catheter 100 can have proximal tubular member 20 extend distally from adapter 110 directly to distal tubular member 24. By way of further example, distal tubular member 24 of catheter 100 can be attached directly to the proximal tubular member 20 without an intervening intermediate section 22, such that distal tubular member 24 has a proximal region secured to the bonding region of proximal tubular member 20. In this manner, the proximal region 24a of distal tubular member 24 can be in an overlapping configuration with the distal region 20b of proximal tubular member 20 to define an overlapping region. Preferably, the overlapping region has a length of approximately 10 cm. Such a device can further improve pushability of catheter 100 and prevent kinking.

In accordance with another aspect of the invention, the elongate main body of the catheter 100 can include a feature for performing a diagnostic, an interventional, or a therapeutic procedure or treatment. Preferably, although not necessarily, such a feature is disposed at least partially at the distal section 106 of the catheter 100. For example, and for purposes of illustration and not limitation, as embodied herein and as depicted in FIG. 1, the elongate main body can further include an inflatable member 114 disposed along a length of the catheter 100. The inflatable member has a proximal end 114a, a distal end 114b, and an inflation chamber 114c bounded by a surface of inflatable member 114. Inflatable member 114 can be made from a variety of materials. For purpose of illustration and not limitation, inflatable member 114 can be made from a polyether block amide ("PEBA"), polyamide, polyurethane, PET, PE, PTFE, polyester, composite materials, or a variety of other materials, including blends. Alternatively, the inflatable member can be made from a polyhydroxyalkanoate including but not limited to poly-4-hydroxybutyrate, available from Tepha Inc., Cambridge, Mass. Inflatable member 114 can be attached to the distal tubular member 24 of catheter 100 by any of a variety of suitable bonding techniques, such as adhesive, fusion, or preferably by welding. Thus, if inflatable member 114 is made of nylon, it is advantageous for distal body portion 24 to be made of a material compatible for a welded or fusion bond therebetween. For the purpose of illustration and not limitation, the inflatable member can be welded to the distal body portion using light energy, adhesive, or heat welding.

In accordance with a further aspect of the invention, catheter can include a first guidewire lumen defined along a length of the catheter and a second lumen defined proximal to the first guidewire lumen along a length of elongate main body of catheter.

For example, and with reference to FIG. 1, catheter 100 is provided with a first guidewire tube 32 having a first guidewire lumen defined therethrough. The first guidewire lumen 32c accordingly can be provided with a proximal guidewire port 32a and a distal guidewire port 32b in fluid communication therewith. Similarly, the catheter 100 is provided with a second guidewire tube 30 having a second guidewire lumen defined therethrough. The second guidewire lumen 30c accordingly can be provided with a proximal guidewire port 30a and a distal guidewire port 30b in fluid communication therewith.

As embodied herein, the first guidewire lumen 32c is disposed along the distal section 106 of the catheter. For example, if an inflatable member 114 is provided, first guidewire lumen 32c extends through the inflatable member with the distal guidewire port 32b located distal the inflatable member and the proximal guidewire lumen located proximal the inflatable member. In a preferred embodiment, inflatable member 114 is positioned on the elongate main body of catheter 100 equidistant between the proximal guidewire port 32a and distal guidewire port 32b, or the distal end of the tip 70, if provided. However, inflatable member 114 can also be placed closer to one port or the other, if desired.

Furthermore, and as embodied herein, the second guidewire lumen 30c is disposed proximal to and spaced from first guidewire lumen 32c. That is, distal guidewire port 30b of second guidewire lumen 30c is spaced proximal from proximal guidewire port 32a of first guidewire lumen 32c. A guidewire inserted proximally distal guidewire port 32b therefore will exit the catheter at proximal port 32a. As illustrated in FIG. 1, proximal guidewire port 32a of first guidewire lumen 32c is preferably axially aligned with distal guidewire port 30b of second guidewire lumen 30c. Advantageously, and as embodied herein and depicted in FIGS. 8 and 9, this arrangement provides an operator with an option to feed guide wire 60 solely through lumen 32c of first guidewire tube 32, as mentioned above and schematically shown in FIG. 8, or alternatively, feed guidewire 60 through each of first guidewire lumen 32c and second guidewire lumen 30c of second guidewire tube 30, as shown in FIG. 9.

Figure 6:
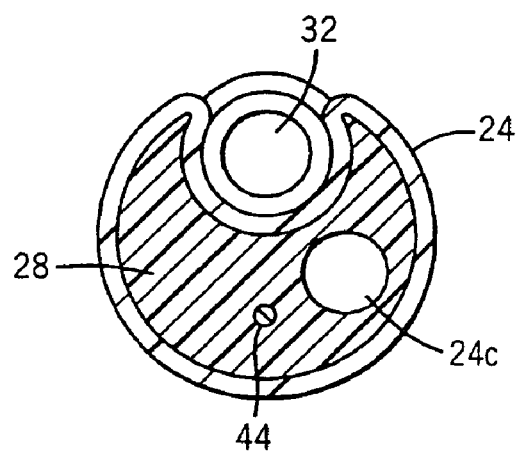
FIG. 6 is a cross sectional view at line 6-6 of the catheter of FIG. 1 in accordance with the present invention.

In a preferred embodiment of the invention, at least the first guidewire lumen 30c is defined by a first guidewire tube 30. The first guidewire tube 30 embodied herein, is joined at its distal end region to the distal end of inflatable member 114 by conventional bonding techniques as depicted in FIG. 1. To anchor the proximal end region of first guidewire tube 32, and in accordance with another aspect of the invention, a circumferential slit is formed in the wall of distal tubular member 24. The wall on the proximal side of the circumferential slit is urged inward, such that the proximal end region 32a of first guidewire tube 32 extends through the slit with the wall of the distal tubular member substantially surrounding the first guidewire tube 32 as depicted in FIG. 6. A reinforcement filler or tube can be provided proximate the slit to anchor and strengthen the joint between the tubular members.

The second guidewire lumen can be formed or defined by a separate tubular member disposed along a length of distal tubular member 24, or can be defined by the distal tubular member 24, itself, as described further below. If formed of a separate tubular member, the second guidewire tube can be anchored at its distal end region to distal tubular member 24 in a manner similar to that of the proximal end region of the first guidewire tube.

Particularly, and as depicted in FIG. 1 in accordance with either aspect of the invention, distal tubular member 24 further includes gap 24d along its length. Gap 24d is in fluid communication with the exterior of catheter 100. For purpose of illustration and not limitation, gap 24d can be constructed by placing two circumferential slits through the wall of distal tubular member 24 to define a flap region. The flap region is depressed toward lumen 24c of distal tubular member 24. As best viewed from FIG. 6, which illustrates a cross section of a portion of catheter 100 at gap 24d, the depressed flap portion is depressed within lumen 24c such that a portion of the wall of distal tubular member 24 has a concave shape. Further, and as schematically shown in FIG. 1, the depressed flap region of distal tubular member 24 is disposed between a first guidewire tube 32 and a second guidewire tube 30. As schematically shown in FIG. 1, second guidewire tube 30 is disposed proximal to gap 24d and first guidewire tube 32 is disposed distal to gap 24d. Advantageously, gap 24d allows fluid communication between the exterior of catheter 100 and both the distal guidewire port 30b of second guidewire lumen 30c, and the proximal guidewire port 32a of first guidewire lumen 32c. Further, and as schematically depicted in FIG. 8, gap 24d provides an exit for a guidewire 60 disposed in the first guidewire lumen 32c, if desired.

As previously stated, a filler material or reinforcement tube 28 can be placed below the gap 24d to strengthen the region proximate the joints. If provided, a mandrel can be inserted during fusion of the members to ensure an inflation lumen is maintained. Additionally, if a stiffening element is provided in the lumen of the tubular member, the filler material provides added material to the sidewall of the tubular member so that the stiffening member does not disrupt the sidewall of the tubular member when the catheter is manipulated during use or during assembly.

The proximal end region of the second guidewire tube, if provided as a separate member, can be secured or anchored in a variety of different manners. For example, and as embodied herein, the proximal end region of second guidewire tube 30 can be secured between the distal end region 22b of intermediate tubular member 22 and the proximal end region 24a of distal tubular member 24 as depicted in FIG. 1. In a preferred embodiment, the distal end region 22b of intermediate tubular member 22, as depicted in FIG. 1, can further include a longitudinal recess such that at least a portion of second guidewire tube 30 is nested within the longitudinal recess of the intermediate tubular member 22. For the purpose of illustration and not limitation, the longitudinal recess can be formed by necking down a distal region of the intermediate tubular member 22 or forming a dimple in of the intermediate tubular member.

Figure 3:
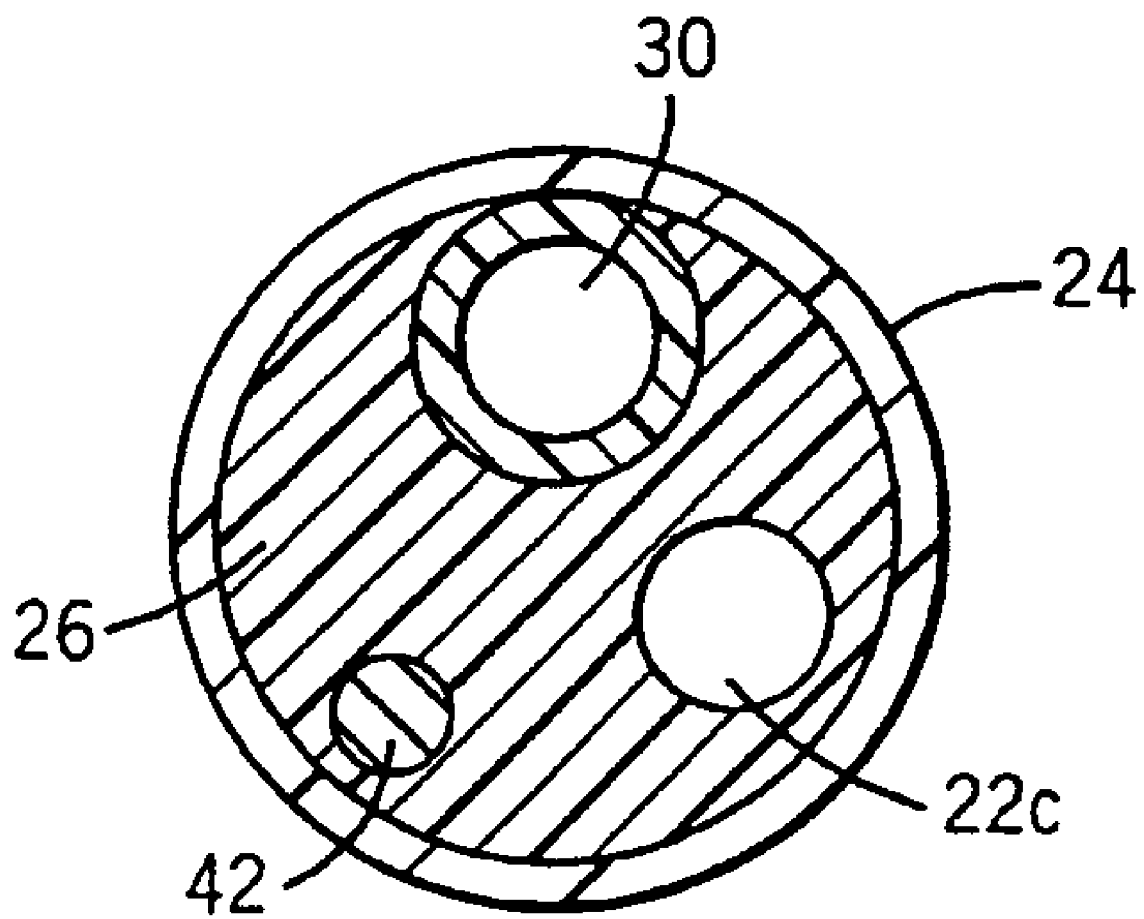
FIG. 3 is a cross sectional view at line 3-3 of the catheter of FIG. 1 in accordance with the present invention.

With the second guidewire tube 30 positioned between the overlapping interface of the intermediate tubular member 22 and the distal tubular member 24, the structure can be fused together to form a joint therebetween. If desired, a filler material or reinforcement tube 26 can be disposed proximate the joint as depicted in FIG. 1. Preferably, a mandrel is located temporarily across the joint when the structure is fused together to define an inflation lumen 22 therethrough, as depicted in FIG. 3.

Alternate constructions for the second guidewire lumen, and the corresponding region, are describe further below.

The material of construction and dimensions for the guidewire lumens will depend upon the intended application. For example, for a cardiovascular catheter, each of the first and second guidewire lumens can be constructed from any suitable polymer such as nylon, PEEK, HDPE, polyimide, PTFE, or PTFE loaded polyimide, polyurethane, polyester, liquid crystal polymer, and the like, including blends or composites thereof. Further, each of the lumens can be made of one or more extruded or pultruded materials, including multilayered co-extrusions or pultrusions, or monolayered material, as discussed below. The first guidewire lumen can have a length of at least approximately 1 cm, and second guidewire lumen can have a length of at least approximately 17 cm.

Catheter 100 can be configured to have proximal guidewire port 30a approximately 10 to 30 cm, and preferably about 20 to 30 cm, proximal to distal tip 70 of catheter 100. Accordingly, catheter 100 can be configured such that guidewire 60 can be disposed through first guidewire tube 32 and exits catheter body at guidewire port 32a of first guidewire tube 32 and then re-enters catheter body 100 at distal port 30b of second guidewire tube 30. Guidewire 60 extends proximally through second guidewire lumen 32c to proximal port 30a.

Alternatively, guidewire 60 can be disposed through guidewire tube 32 and exit catheter 100 through proximal guidewire port 32a at gap 24d. Proximal guidewire port 32a is preferably disposed near the proximal end 114a of inflatable member 114. For example and not limitation, proximal port 32a can be disposed approximately 8 cm proximal to distal tip 70. Alternatively, the proximal port 32a can be disposed at a variety of other distances from distal tip 70, depending upon the length of the inflatable member 114 or the intended application. In one preferred embodiment, the length between inflatable member 114 and proximal guidewire port 32a is substantially the same as the distance between inflatable member 114 and distal guidewire port 32b.

Generally, first guidewire tube 32 is shorter in length than second guidewire tube 30. For example and not limitation, first guidewire tube 32 can have a length of at least approximately 3 to 4 cm; although generally is dependent at least on the length of inflatable member 114. Second guidewire tube generally has a length of approximately 10 to 30 cm, and preferably about 21 to 23 cm, depending on the length of the inflatable member 114. Preferably, the outer diameter of first and second guidewire tubes, 32 and 30, respectively, are approximately 0.55 mm, and the inner diameter of first and second guidewire tubes, 32 and 30, respectively, are approximately 0.42 mm. However, it should be recognized that each of first guidewire tube 32 and second guidewire tube 30 can have any suitable length and dimension, as desired.

A variety of materials can be used to form first guidewire tube 32 and second guidewire tube 30. For example and not limitation, either first guidewire tube 32 or second guidewire tube 30 can be formed of polymers such as polyamide, PEEK, HDPE, PEBAX®, Polyurethane, and the like, including blends thereof. Alternatively, either the first or second guidewire tube can be formed from a composite or formed member. For example and not limitation, either guidewire tube can be made of one or more extruded or pultruded materials, dip molded materials, polymeric loaded materials, or shrink fitted materials, as described above. As yet another alternative, either the first or second guidewire tube can be formed of fiber reinforced materials.

In one preferred embodiment, second guidewire tube 30 is formed of a multi-layered co-extrusion, and first guidewire tube 32 is formed of a monolayer polymeric material. For example and not limitation, second guidewire tube 30 can be formed of at least a two-layer material including an inner polymeric layer and an outer polymeric layer.

Preferably, the inner layer is a lubricious material and facilitates gliding of guidewire 60 through guidewire lumen. Alternatively, the inner material can have a lubricous coating, for example, with a silicone coating.

In one preferred embodiment, the second guidewire tube is formed of an inner layer including HDPE and an outer layer including a polyamide, such as nylon. However, alternative materials can be used for either the inner layer or the outer layer as known in the art. For example, the inner layer can alternatively be formed from materials such as polyimide, PTFE, or PTFE loaded polyimide and the outer layer can be formed from materials including nylon, nylon copolymers including Pebax®, Hytrel®, polyolefin, polyurethane, and blends thereof. Alternatively, other suitable materials can be used as known in the art.

The inner layer can be secured to the outer layer by various suitable methods and structures, which depend on the particular selection of the inner layer material and the outer layer material, as known in the art. For example, the inner layer can be secured to the outer layer by a mechanical bond, chemical bond, or other bonding means such as mechanical friction fit. For example and not limitation, a lubricious inner layer of HDPE is mechanically bonded to an outer layer of nylon.

As mentioned above, guidewire tube 32 is preferably formed of a monolayer polymeric material. As depicted in FIG. 1, distal end of inflatable member 114 is secured to first guidewire tube 32. Accordingly, the particular material selected for the first guidewire tube 32 should be compatible with the material selected for the inflatable member 114. Preferably, first guidewire tube 32 is formed of a monolayer of nylon, and inflatable member 114 is a nylon balloon, such that a fusion bond can be formed therebetween. Alternatively, the inflatable member can be adhesively bonded to the first guidewire tube. Alternatively, both members can be formed of a PEBA material. Furthermore, the first guidewire tube can be formed of a multi-layer tubular member, if desired.

In further accordance with the invention, distal tip 70 can be secured to first guidewire tube 32. As depicted, distal tip 70 is in an overlapping configuration with the distal end of first guidewire tube 32. In one embodiment, distal tip is configured to abut the distal end of inflatable member 114. Alternatively, however, distal tip 70 can be configured to overlap the distal end of inflatable member 114. Preferably, distal tip 70 is secured to the distal end of first guidewire tube by heat welding. However, other methods can be used such as using adhesives, or the like.

A variety of materials can be used to form distal tip 70. Preferably, distal tip 70 is formed of a material having a durometer less than the durometer of the distal tubular member 24. For example and not limitation, distal tip 70 can be formed of polyamides, including nylon, polyether block amide, high density polyethylene, polyurethane, polyesters, including HYTREL. The particular selection of the material for the distal tip 70, however, is depending on the desired application of catheter 100.

As previously noted, the second guidewire lumen can be formed by a second guidewire tube or by other construction. For example, FIG. 1 depicts a catheter with second guidewire lumen 30c defined by second guidewire tube 30. The proximal guidewire port 30a is defined wholly by the proximal end region of second guidewire tube 30 due to the joint configuration previously described. In this manner, and by using a tubular member with a lubricious inner layer, placement of the catheter relative to the guidewire can be enhanced.

Figure 4C:
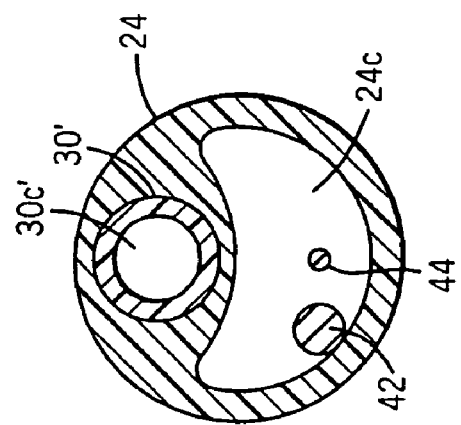
FIG. 4C is another cross sectional view at line 4-4 of the catheter of FIG. 1 in accordance with an embodiment of the present invention.

Between the proximal guidewire port 30a and the distal guidewire port 30b, the second guidewire lumen 30c can be disposed either in a coaxial relation or a side-by-side relation with the inflation lumen 24c, or even a hybrid of the two. For the purpose of illustration and not limitation, FIG. 4A depicts a cross section of a portion of catheter 100 in which second guidewire tube 30 is disposed generally coaxially within distal tubular member 24, such that inflation lumen 24c annularly surrounds guidewire tube 30 and guidewire lumen 30c.

Figure 4B:
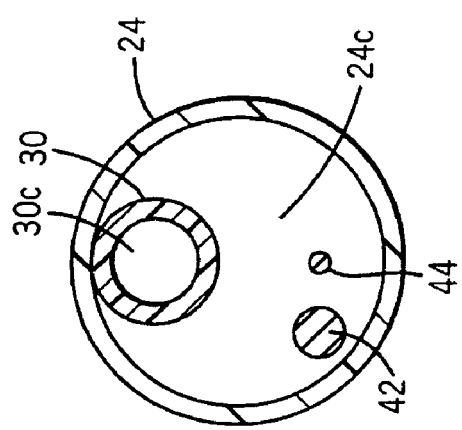
FIG. 4B is an alternate cross sectional view at line 4-4 of the catheter of FIG. 1 in accordance with an embodiment of the present invention.
Figure 4A:
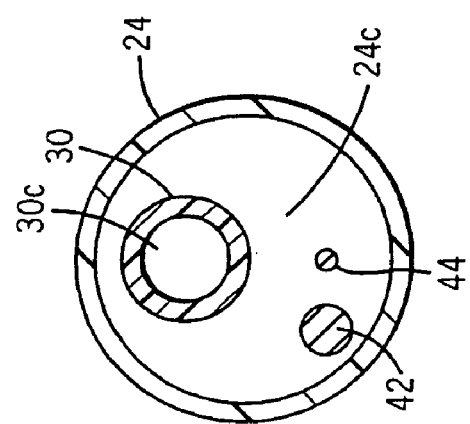
FIG. 4A is a cross sectional view at line 4-4 of the catheter of FIG. 1 in accordance with an embodiment of the present invention.
Figure 5:
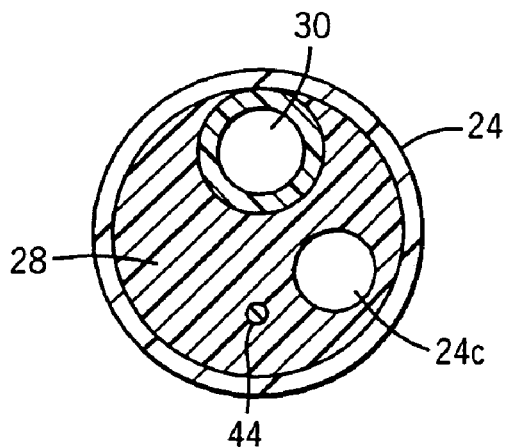
FIG. 5 is a cross sectional view at line 5-5 of the catheter of FIG. 1 in accordance with the present invention.

Alternatively, as embodied herein, and as depicted in FIG. 4B, catheter 100 can include a modified, dual lumen configuration. That is, second guidewire tube 30 can be secured by any suitable bonding technique along all or a portion of its length to a longitudinal inner surface of distal tubular member 24. Accordingly, inflation lumen 24c surrounds only a portion of guidewire tube 30. In one preferred aspect of the invention, a light absorption welding technique of EP 1435252, the contents of which are incorporated herein by reference herein, can be used.

In yet another alternative, as embodied herein and as depicted in FIG. 4C, catheter 100 can be configured to include a conventional dual lumen configuration along at least a portion of the intermediate region 104. The term "conventional dual lumen configuration" refers to a configuration in which guidewire lumen 30c' and inflation lumen 24c are arranged generally in parallel and side-by-side relationship. Such dual lumen configurations are available as a single extrusion of suitable polymer-material, such as nylon or the like. If desired, and as illustrated in FIG. 4C, second guidewire tube can further include at least a portion 30' formed of a lubricious tube or liner, such as HDPE, PTFE, PEEK or the like. As depicted in FIG. 4C, inflation lumen 24c can be configured to have a crescent or generally semi-circular shaped cross-section. Such a semi-circular shaped cross section is advantageous because it maximizes the cross sectional area of inflation passage 24c, thus minimizing flow resistance to inflate inflatable member 114.

Alternatively, the dual lumen member can be constructed by dipping, shrink fitting, melting or fusing two or more tubular members together. For example, and not limitation, the second guidewire tube and an inflation tube can each be formed by a suitable liner. The guidewire tube liner and the inflation tube liner are arranged generally in a parallel and side-by-side relationship within a polymeric tubular member. The assembly is then heated to a temperature to cause the polymeric tubular member to melt around a substantial portion of each of the second guidewire tube liner and the inflation tube liner to secure the liners in a dual lumen configuration. A removable shrinkwrap can be used to shape the outer surface of the member during the fusion process.

If the distal tubular member 24 is formed at least in part by a dual lumen member, as described above, then a number of different joint configurations can be used in accordance with the invention. For example, and as embodied herein and depicted in FIG. 10, the distal end region 22b of intermediate tubular member 22 can be provided in an overlapping configuration with the proximal end region 24a of distal tubular member 24. At least a portion of distal tubular member includes a guidewire lumen 30c and an inflation lumen 24c in a side-by-side configuration.

Figure 14A:
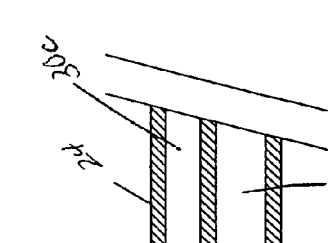
FIGS. 14A to 14G is a schematic representation of a method to manufacture the catheter of FIG. 10 in accordance with the present invention.
Figure 14B:
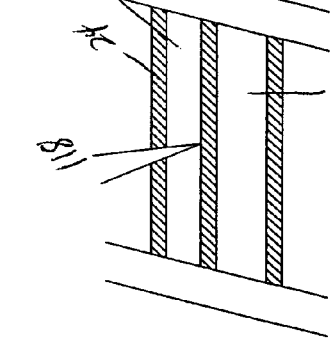
Figure 14C:
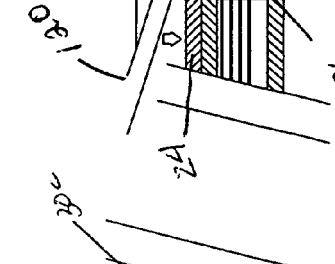
Figure 14D:
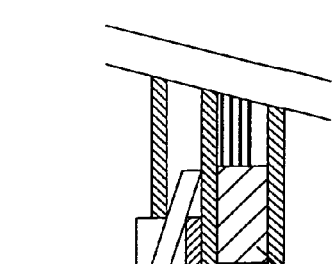
Figure 14E:
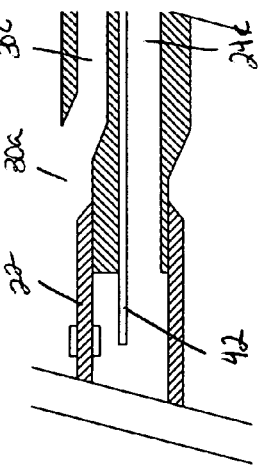

To be received within the distal end region of intermediate tubular member 22, at least the proximal end region of the dual lumen member can be collapsed, such as depicted in FIGS. 14A through 14G, and particularly in FIGS. 14C to FIG. 14E, described further below. Alternatively, the distal end region of intermediate tubular member 22 can be received within the proximal end region of the dual lumen member, as depicted in FIGS. 17A to 17G, an particularly in FIG. 17E.

Distal tubular member 24 further includes at least one first filler material or reinforcement member 26 within the inflation lumen 24c proximate the joint between the intermediate and distal members. A cross sectional view of catheter 100 at line 11-11 of FIG. 10, as depicted in FIG. 11, demonstrates that intermediate stiffening member 42, as described further below, can be embedded in material of reinforcement member 26 after fusion to form a joint therebetween. As depicted in the cross sectional view of catheter 100 in FIG. 12, the dual lumen member transitions distally to define a portion of the catheter 100 that includes guidewire lumen 30c and inflation lumen 24c. To strengthen the joint, filler material or a reinforcement tube is provided, and a removable mandrel is disposed prior to fusion such that inflation lumen 24c having a circular or crescent-shaped cross section is formed, as demonstrated in FIG. 12. Ultimately, the dual lumen member transitions to a conventional configuration with guidewire lumen 30c and inflation lumen 24c in a side-by-side relationship with inflation lumen 24c having a crescent or substantially semi-circular cross section, as demonstrated in FIG. 13.

For the purpose of illustration and not limitation, the catheter 100 of FIG. 10 can be manufactured by the steps schematically and sequentially depicted in FIGS. 14A to 14G.

As demonstrated in FIGS. 14A and 14B, a partial circumferential cut 118 is made in a dual lumen member 24 to define proximal guidewire port 30a. A series of removable mandrels 120 are used to maintain the lumens and port of the dual lumen structure, as desired, during the heating and fusion steps, as depicted in the Figures. For the purpose of illustration, a removable mandrel 120 can be inserted into the defined proximal guidewire port 30a and along guidewire lumen 30c. Another removable mandrel 120 can be inserted into the inflation lumen, as depicted in FIG. 14C. The proximal region of the dual lumen member 24 can be collapsed to configure the opening of proximal guidewire port 30a, as depicted in FIG. 14C. A removable shrink tubing 124 can be applied to the dual lumen member 24. The assembly can be heated to form proximal guidewire port 30a and to connect the collapsed proximal end of dual lumen member 24 to the guidewire lumen sidewall, as depicted in FIGS. 14D.

Figure 14F:
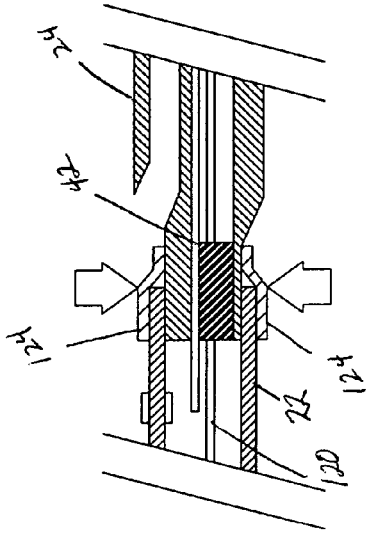

As previously described, and as shown in FIGS. 14C and 14F, a reinforcement member 26 can be inserted along the elongate main body to secure the stiffening member within the lumen of the elongate main body. Additionally, a mandrel is provided along the elongate main body to define at least a portion of the inflation lumen through the reinforcement member 26.

Figure 14G:
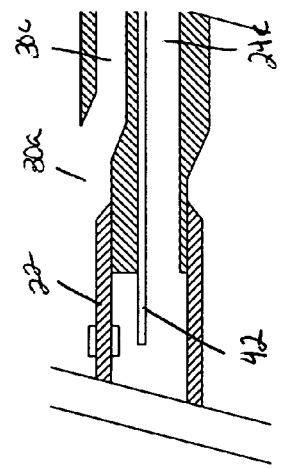
Figure 16:
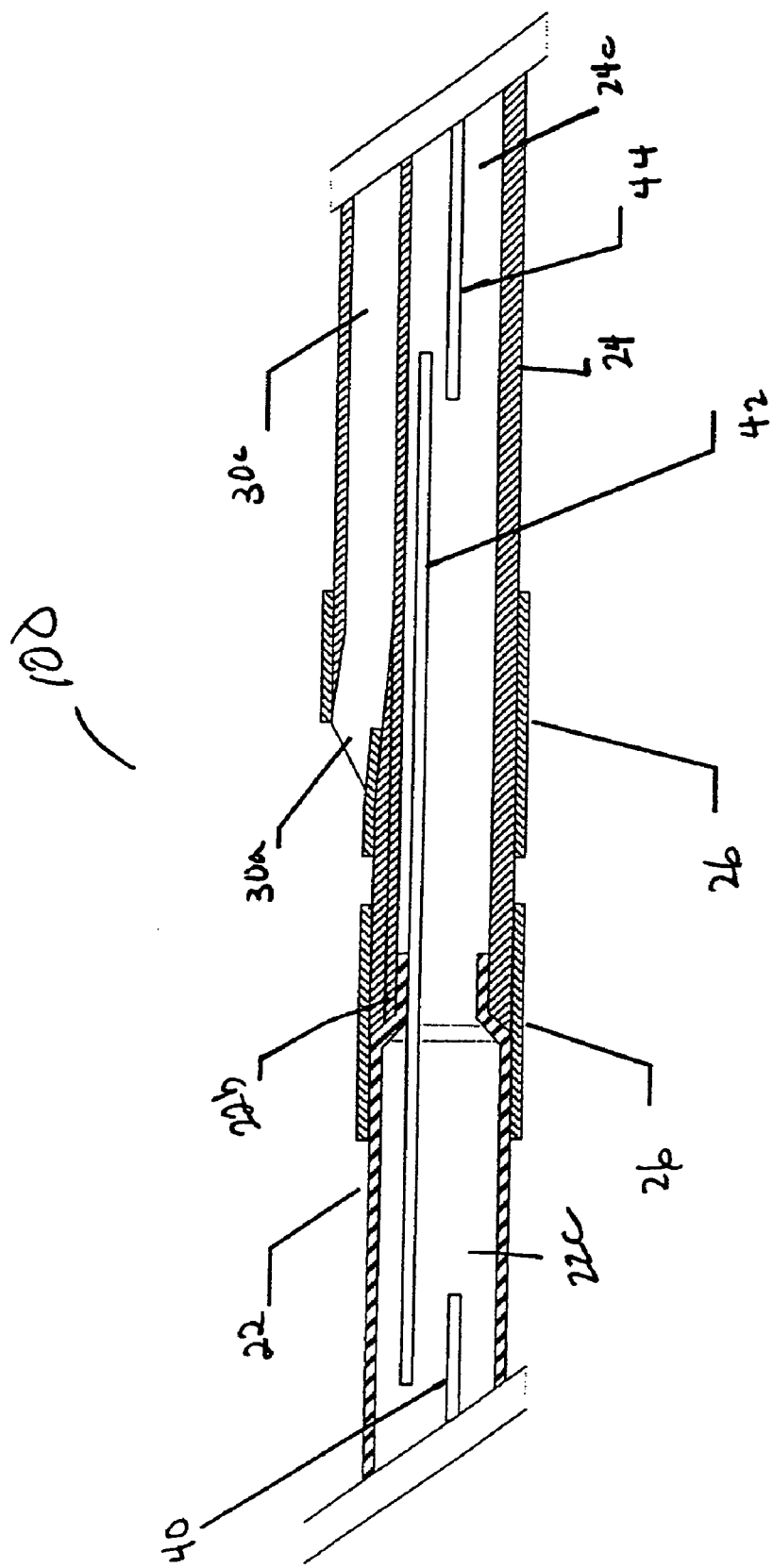
FIG. 16 is a schematic representation of the embodiment of FIG. 15 in accordance with the present invention.

As depicted in FIGS. 14E and 14F, the intermediate tubular member 22 can be secured to the proximal end of the dual lumen tubular member by applying a removable shrink tube 124 and appropriate application of heat to fuse the members together. FIG. 14G depicts the catheter 100 including formed proximal guidewire port and joint configuration.

Alternatively, as demonstrated in FIG. 16 and FIGS. 17A to 17G, and in particular FIG. 17E, the distal end region 22b of intermediate tubular member 22 having reduced cross dimension can be received and secured within proximal end region 24a of distal tubular member 24. To accomplish this configuration, and in accordance with the another aspect of the invention, the assembly depicted in FIG. 15 can be manufactured by the steps schematically and sequentially depicted in FIGS. 17A to 17G. Particularly, and in lieu of or in addition to disposing reinforcement members 26 within the lumen at the joint, the assembly, as depicted in FIG. 15, includes at least one first reinforcement member 26 placed about at least one of distal tubular member 24 or intermediate tubular member 22 as viewed in FIG. 16 and FIG. 17F. As illustrated, the distal member and the intermediate member can be secured by applying a removable heat shrink tube 124 and appropriate heat to fuse the members together. FIG. 17G depicts the catheter 100 including the alternative formed proximal guidewire port and joint configuration with mandrel 120 removed.

Although reference has been made to alternative methods and configurations for joining the proximal end of the dual lumen member to the intermediate tube, such methods and configurations also can be used for joining the distal end of the dual lumen member to an adjacent tubular member as desired. For example, the distal end of the dual lumen member can be attached to the first guidewire lumen and either an outer distal tube member or directly to the balloon using the methods similar to that of FIGS. 14A-14G or FIG. 16, so as to define a configuration similar to that depicted in FIGS. 5-6 at region 28a.

Furthermore, inflation lumen 24c and/or guidewire lumen 30c can be configured to have any of a variety of cross-sectional shapes. For example and not limitation, the cross-sectional shape inflation lumen 24c can be substantially elliptical, substantially rectangular, or be defined by a polygon (e.g., a hexagon), among others.

Figure 7:
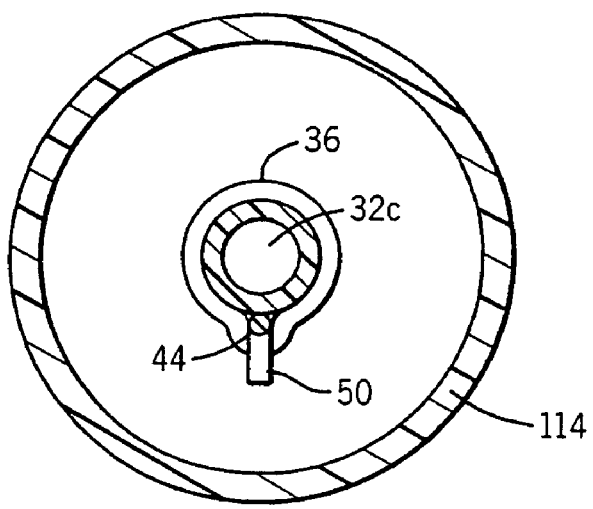
FIG. 7 is a cross-sectional view at line 7-7 of the catheter of FIG. 1 in accordance with the present invention.

In further accordance with a further aspect of the invention, and as noted above, first guidewire tube 32, as illustrated in FIG. 7, can be arranged in a coaxial arrangement at least with a portion of inflatable member 114. Thus, in accordance with a further aspect of the invention, catheter 100 can be configured to include a transition along at least a portion of its length. In particular, catheter 100 can have a first segment along its length in which second guidewire tube 30 is arranged in a side-by-side configuration or a modified, side-by-side configuration, and a second segment in which first guidewire tube 32 is arranged in a coaxial configuration. Accordingly, it is an aspect of the present invention to include a catheter 100 having a transition along at least a portion of its length.

Further in accordance with another aspect of the invention, the second guidewire lumen can be configured to be entirely in a coaxial relationship with inflation lumen along the length therebetween the proximal guidewire port 30a and the distal guidewire port 30b, or entirely in a side-by-side relation therebetween, or a combination of the two. That is, a portion of the length of the distal tubular member 24 can be formed of a dual lumen member, as described, with an additional portion of the distal tubular member formed of an outer tubular member and an inner tubular member in coaxial relationship, such that at least the inner tubular member is joined in fluid communication with one of the lumens of the dual lumen member.

In accordance with a further aspect of the invention, the catheter can include an elongate main body having one or more stiffening members. The term "stiffening member" can include a filament, strand, wire, coil, or other member to increase the stiffness of a section of the catheter elongate main body. Preferably, however, the stiffening member is a wire member.

In a preferred embodiment, and in accordance with an additional aspect of the invention, two or more overlapping stiffening members are provided. Particularly, and as embodied herein and schematically depicted in FIG. 1, catheter 100 can include proximal, intermediate, and distal stiffening members, 40, 42, and 44, respectively.

Proximal stiffening member 40 has a proximal end 40a, a distal end 40b, and a midpoint therebetween. The midpoint is preferably equidistant from the proximal end and the distal end of the stiffening member. In one embodiment, proximal stiffening member 40 has a proximal end secured to adapter 110 and a length sufficient extend distally through and beyond lumen 20c of proximal tubular member 20. The distal end of proximal stiffening member is freely floating or unattached to the catheter main body. The proximal stiffening member 40 can be secured to the adapter by adhesive, welding, or alternatively, can be embedded into the adapter during an injection molding process.

As illustrated in FIG. 1, proximal stiffening member 40 can include a taper or stepped region of increasing cross dimension. For example and not limitation, FIG. 1 demonstrates that proximal stiffening member is configured to have a stepped region with the transition located within the proximal tubular member 20. However, proximal stiffening member 40 can be configured to include a taper, if desired, which extends along a portion of the entire length of the member. For example, proximal stiffening member can have a length of approximately 110 to about 125 cm and include a first section having an outer diameter of about 0.1 mm, a second section having an outer diameter of 0.2 mm, and a third section having an outer diameter of about 0.3 mm. However, it should be recognized that other dimensions can be used. In a preferred embodiment, the stiffening member has a length disposed in the proximal tubular lumen 20c such that the transition from a larger outer diameter to a smaller outer diameter is proximal to the distal end region 20b of proximal tubular member 20.

Alternatively, as schematically depicted in FIG. 2, proximal stiffening member 40 can be secured to the elongate main catheter body of catheter 100 such that at least a proximal portion of the stiffening member 40 is freely-floating or unsecured within the proximal tubular member 20. For example and not limitation, and intermediate location, such as the midpoint, or the distal end of proximal stiffening member 40 can be secured to intermediate tubular member 22 or another member of the main body.

In yet another alternative, proximal stiffening member 40 can have at least one of the proximal end or distal end secured to its proximal tubular member 20. For example and not limitation, if the proximal tubular member is formed of metal, proximal stiffening member 40 can be welded, brazed, or soldered at or near the distal end of proximal tubular member 20 or to a region proximal to the distal end of proximal tubular member 20.

FIG. 1 further depicts intermediate stiffening member 42 having a proximal end 42a and a distal end 42b and a length therebetween. Intermediate stiffening member 42 can be secured to at least one region of the elongate main body of catheter 100. For example, and not limitation, intermediate stiffening member 42 can be disposed in inflation lumen 22c and secured at an intermediate location to an inner surface of intermediate tubular member 22. In this regard, the distal end 42b and the proximal end 42a of intermediate stiffening member 42 can each be configured to freely-float within the lumen 22c. As another illustrative example, intermediate stiffening member 42 can be secured at at least one of its proximal end or its distal end to a region of the elongate main body of catheter 100. Preferably, and as illustrated in FIG. 1, intermediate stiffening member 42 is secured within filler material or reinforcement member 26.

Preferably, as embodied herein and depicted in FIG. 1, intermediate stiffening member 42 is in an overlapping configuration with a portion of proximal stiffening member 40. That is, the distal end 40b of proximal stiffening member 40 preferably extends distally beyond the proximal end 42a of intermediate stiffening member 42. More preferably, the stiffening members are in non-connected relationship.

Distal stiffening member 44 has a body including a proximal end 44a, a distal end 44b, and a length therebetween. As demonstrated in FIG. 1, can best be viewed in FIGS. 4A, 4B, and 4C, distal stiffening member 44 is in an overlapping configuration with a portion of intermediate stiffening member 42 and extends distally to a region near or into inflatable member 114. Distal stiffening member 44 can be secured to at least one region of the elongate main body of catheter 100. For example, and not limitation, distal stiffening member 44 can be disposed in inflation lumen 24c and secured at an intermediate location to an inner surface of distal tubular member 24. In this regard, the distal end 44b and the proximal end 44a of distal stiffening member 44 can be secured at at least one of its proximal end or its distal end to a region of the elongate main body of catheter 100. Preferably, and as illustrated in FIG. 1, distal stiffening member 44 is secured within filler material or reinforcement member 28.

As embodied herein and depicted in FIGS. 1 and 7, and further in accordance with another aspect of the invention, catheter 100 includes at least one radiopaque marker band 36 affixed to a surface of first guidewire tube 32. As depicted in FIG. 7, marker band 36 includes a keyway in which the distal end region of distal stiffening member 44 is slidingly disposed. Accordingly, distal stiffening member 44 is slidingly engaged within marker band 36 to facilitate flexing, and can extend distal to marker band 36. Preferably, distal stiffening member 44 further includes a stopper 50 or protrusion to increase pushability of catheter 100. Alternatively, the distal stiffening member 44 can also terminate at the proximal end of inflatable member 114.

In an alternative embodiment, as schematically depicted in FIG. 2, catheter 100 can include only a proximal stiffening member 40 and a distal stiffening member 44. As shown in FIG. 2, distal stiffening member 44 extends proximally from marker band 36 to proximal stiffening member 40. Distal stiffening member 44 is in an overlapping configuration with a portion of proximal stiffening member 40. Alternatively, a single stiffening member can be provided, which extends distally from proximal tubular member 20 to a desired location along the length of the main body. The single stiffening member can be secured at its proximal end or, more preferably, at an intermediate or distal location along its length.

Generally, the length of each stiffening member 40, 42, and 44, and the material used to form each stiffening member is dependent upon the desired stiffness for each portion of the catheter body. Additionally, the length of each stiffening member will be dependent on the total number of stiffening members. For example and not limitation, if catheter 100 has three stiffening members, proximal stiffening member 40 can generally have a length of approximately 110 to 125 cm. Preferably, proximal stiffening member 40, as illustrated in FIGS. 1 and 2, terminates proximal to guidewire port 30a. Intermediate stiffening member 42 generally has a length of about 5 to 15 cm. As depicted in FIG. 1, intermediate stiffening member 42 preferably extends across guidewire port 30a. Distal stiffening member 44 generally has a length of approximately 5 to 30 cm and preferably, greater than 10 cm. Preferably, distal stiffening member extends proximally across gap 24d. If only proximal stiffening member 40 and distal stiffening member 44 are used, at least one stiffening member would have a greater length. Further, at least one stiffening member can have either a proximal taper, a distal taper, or both.

A variety of materials can be used for each stiffening member 40, 42, and 44, respectively. For example and not limitation, a stiffening member can be formed of stainless steel, nitinol, titanium, tantalum, Eligiloy, cobalt, chrome, nickel and any combination thereof. Additionally, synthetic materials can be used including carbon, carbon fiber, glass fiber, aramid fiber, boron fiber, Dacron® and/or Kevlar®, available from E.I. du Pont de Nemours and Company. Each stiffening member can be formed of a different material or each can be formed of the same material. Alternatively, at least two stiffening members can be formed of different material. For the purpose of illustration, proximal stiffening member can be formed of stainless steel 40, intermediate stiffening member 42 can be formed of a carbon material or carbon reinforced material, and distal stiffening member 44 can be formed of nitinol.

Depending upon the materials of construction, and the intended use of the catheter, it can be beneficial to further reinforce the ports along the length of the catheter 100 or seal the inflation-deflation lumen at the guidewire ports. Hence, in further accordance with the invention, and as schematically depicted in FIG. 1, catheter 100 can further include a first reinforcement member 26 and a second reinforcement member 28 disposed adjacent to proximal guidewire port 30a and gap 24d, respectively.

For the purpose of illustration and not limitation, first reinforcement member 26 is disposed in lumen 22c adjacent to proximal guidewire port 30a and defines reinforcement region 26a. Additionally, second reinforcement member 28 is disposed in inflation lumen 24c adjacent to distal guidewire port 24d, and defines reinforcement region 28a, as demonstrated in FIGS. 1 and 2. Each reinforcement member is melted upon formation of the corresponding joint, as previously described.

At least one of the first or second reinforcement members 26,28 can be in the form of a polymeric member formed of materials such as for example and not limitation, polyamide, PEEK, polyether ketone, polyketone. Preferably, at least one of first and second reinforcement members is a nylon tubular member.

As mentioned, first reinforcement member 26 and second reinforcement member 28 form first reinforcement region 26a and second reinforcement region 28a, respectively. For the purpose of illustration, a mandrel made of non-stick material, such as PTFE, and preferably having a desired shape corresponding to a lumen is slid within the lumen of the tubular reinforcement member. Additionally, if desired, a corresponding stiffening member can also be inserted in the lumen of the tubular reinforcement member. For example, intermediate stiffening member 42 can be disposed in the reinforcement member 26, and distal stiffening member 44 can be inserted in the lumen of second tubular reinforcement member 28. A shrink tube can be placed over the welding zone and the assembly is then heated. The application of heat will act to melt the polymer material, and cause the molten polymer of the first tubular reinforcement member 26 to form a first reinforcing region 26a, and cause the molten polymer of the second tubular reinforcement member 28 to form second reinforcing region 28a.

As illustrated in FIG. 3, after fusing or melting first reinforcement member 26, for example by applying heat, the mandrel is removed, and inflation lumen 24c is defined (by the mandrel), and the molten polymer which corresponds to first reinforcement region 26a causes intermediate stiffening member 42 to become embedded within reinforcing region 26a. Similarly, as depicted in FIG. 6, inflation lumen 24c is defined and a portion of distal stiffening member 44 is embedded within reinforcement region 28a, which is defined by the molten polymer of second reinforcement member 28. Advantageously, each of reinforcement region 26a and 28a can act to reinforce or support a length of elongate main body of catheter 100, and also to secure stiffening member 42 and stiffening member 44, respectively. Further, the reinforcement region can act to seal the inflation lumen at the guidewire ports.

A variety of types of medical devices are suitable for delivery by the catheter of the present invention. For purpose of example and not limitation, a medical device can be provided, for example, in the form of a balloon-expandable stent (not shown). Such devices are generally well known in the art. However, the catheter of the present invention is not limited to the delivery of balloon expandable stents. Other devices may also be used. For example, stent-grafts, bifurcation systems, coils, filters, heart valve repair devices, and embolic protection devices may be delivered within a patient's vasculature using catheter 100 of the present invention. Other devices such as a prosthesis retrieval mechanism, antennae for intravascular MRI, or visual or ultrasonic imaging devices can also be delivered or used with catheter at a predetermined location in a patient's luminal systems. Moreover, combinations of medical devices and/or beneficial agents or pharmaceutically active agents can also be delivered using the device of the present invention. For example, multiple stents or a combination of stents and embolic protection devices and/or beneficial agents can be delivered using catheter of the present invention, mounted on separate inflatable members (not shown).

Although reference has been made to a catheter having an inflatable member 114 at its distal body section, a variety of other structures for delivering to or use within a luminal system can be provided. For example, if desired, it is also possible to deliver self-expanding medical devices on a catheter of the invention. In accordance with this aspect of the invention, a medical device in the form of a self-expanding prosthesis, such as a self-expanding stent, can be provided. If a self-expanding medical device is to be delivered using the catheter of the invention, it may be necessary to provide a restraint device to restrain expansion of the medical device, and permit deployment at the appropriate time by a physician. Such a restraint device can take the form of a retractable sheath having a proximal end, a distal end, an inner surface and an outer surface. Sheath can be withdrawn proximally so as to deploy the medical device by actuating an actuator (not shown). The actuator can be a simple push-pull actuator, a gear mechanism, or a hydraulic actuator, spring loaded actuator, or pneumatic actuator. Alternatively, the actuator can be electrically or chemically driven artificial muscle, which is based on contractile alloys or polymers. For example and not limitation, the contractile alloys can be Flexinol, available from Dynalloy Inc. Costa Mesa, Calif., or polyacrylonitrile-polypyrrole- or polyvinylalcohol-fibers. The actuator can be attached to sheath directly at proximal end of sheath, or may be attached by a pull wire. Alternatively, the actuator can be attached to a unravel-able system, such as a knitted member. Such actuators are provided in, for example, U.S. Pat. No. 6,425,898 to Wilson, U.S. Pat. No. 5,906,619 to Olson, U.S. Pat. No. 5,772,669 to Vrba and U.S. Pat. No. 6,527,789 to Lau et al., each of which is incorporated by reference herein in its entirety.

A variety of other restraint devices can additionally or alternatively be used. For example, restraint bands (not shown) could alternatively be used that are retracted proximally by a pull wire attached to an actuator. Similarly, restraint device can take the form of a frangible envelope (not shown) with a pull wire embedded within the wall of the envelope. Self expanding medical device can accordingly be deployed by actuating actuator, which pulls back on the pull wire, splitting open the frangible envelope, resulting in deployment of the self-expanding device. Other possible actuators (e.g., thermal actuation, wire restraints, balloon-ruptured restraints and the like) are also possible and within the scope of the invention.

In accordance with another aspect of the invention and as previously described in conjunction with certain aspects of the invention, a method of performing a medical procedure is provided. The method includes providing a catheter as described herein, disposing a guidewire within a lumen of a patient, and inserting the guidewire through at least one of the first guidewire lumen and the second guidewire lumen of the catheter.

The method in accordance with the invention can also include providing and inflating an inflatable member in a lumen of a patient, retracting the guidewire until a distal extremity of the guidewire is proximal to the proximal guidewire port 30a of the intermediate section 104 of the catheter, and allowing blood to perfuse through the first guidewire lumen of the distal body portion.

The methods and systems of the present invention, as described above and shown in the drawings, provide for a catheter with superior properties including superior flexibility and pushability. It will be apparent to those skilled in the art that various modifications and variations can be made in the device and method of the present invention without departing from the spirit or scope of the invention. Thus, it is intended that the present invention include modifications and variations that are within the scope of the appended claims and their equivalents.

We claim:

1. A catheter comprising:
   an elongate main body including at least a proximal section and a distal section;
   a first guidewire lumen disposed along at least a portion of the distal section of the elongate main body and having a proximal guidewire port and a distal guidewire port;
   a second guidewire lumen disposed along the elongate main body proximal the first guidewire lumen and having a proximal guidewire port and a distal guidewire port, the distal guidewire port of the second guidewire lumen spaced proximally from the proximal guidewire port of the distal guidewire lumen to define a gap therebetween, wherein the proximal guidewire port of the first guidewire lumen and the distal guidewire port of the second guidewire lumen are each in communication with an exterior of the catheter via the gap; and
   a stiffening member extending across the gap.

2. The cathet er of claim 1, wherein the stiffening member is a wire.

3. The catheter of claim 1, wherein the stiffening member is made of metal, metal alloy, polymer, composite, carbon, and carbon reinforced material.

4. The catheter of claim 1, wherein the stiffening member is a carbon tubular member.

5. The cathet er of claim 1, wherein the stiffening member is made of filler material.

6. The catheter of claim 1, wherein the proximal port of the first guidewire lumen is axially aligned with the distal port of the second guidewire lumen.

7. The catheter of claim 1, wherein each of the distal port of the second guidewire lumen and the proximal port of the first guidewire lumen is in fluid communication with the exterior of the catheter.

8. The catheter of claim 1, wherein the gap has a length sufficient to accommodate exit or entry of a guidewire.

9. The catheter of claim 1, further including an inflatable member located proximate the distal section of the catheter.

10. The catheter of claim 9, wherein the inflatable member is formed from a material selected from the group consisting of polyamide, polyamide block copolymers, polyester, polyester block copolymers, polyurethane, polyurethane block copolymers, polycarbonate block copolymers, grafted polymers, and biopolymers, and any blend thereof.

11. The catheter of claim 9, wherein the inflatable member has a proximal end secured to the distal section of the catheter and a distal end secured to a first guidewire tube defining the first guidewire lumen.

12. The catheter of claim 9, wherein the inflatable member is centrally located between the distal port and the proximal port of the first guidewire lumen.

13. The catheter of claim 9, wherein at least a portion of the first guidewire lumen extends through an interior of the inflatable member.

14. The catheter of claim 13, wherein the distal port of the first guidewire lumen is distal to the inflatable member.

15. The catheter of claim 1, wherein the first guidewire lumen is defined by a first guidewire tube, and the distal section of the catheter is defined at least partially by a distal tubular member, the distal tubular member and the first guidewire tube being arranged at least partially in a coaxial configuration.

16. The catheter of claim 15, wherein the first guidewire tube is formed from a monolayer polymeric material.

17. The catheter of claim 1, wherein the second guidewire lumen is defined by a second guidewire tube, and the distal section of the catheter is defined at least partially by a distal tubular member, the distal tubular member and the second guidewire tube being arranged at least partially in a side-by-side configuration.

18. The catheter of claim 17, wherein the second guidewire tube is formed from a multilayer polymeric material.

19. The catheter of claim 17, wherein the second guidewire tube is within the distal tubular member.

20. The catheter of claim 19, wherein at least a portion of an outer surface of the second guidewire tube is attached to at least a portion of an inner surface of the distal tubular member.

21. The catheter of claim 1, wherein the main elongate body of the catheter has a multi-lumen member disposed at least partially between the proximal port and the distal port of the second guidewire lumen, at least one lumen of the multi-lumen member defining the second guidewire lumen.

22. The catheter of claim 21, wherein the multi-lumen member is an extruded member.

23. The catheter of claim 1, further including an intermediate section disposed between the proximal section and the distal section of the catheter.

24. The catheter of claim 23, wherein the proximal guidewire port is disposed in a region of the intermediate section.

* * * * *